United States Patent [19]

Stetter et al.

[11] Patent Number: 4,770,692
[45] Date of Patent: Sep. 13, 1988

[54] 4-CYANO(NITRO)-5-OXY(THIO)-PYRAZOLE DERIVATIVES, COMPOSITION CONTAINING THEM, AND HERBICIDAL AND PLANT GROWTH REGULATING METHODS OF USING THEM

[75] Inventors: Jörg Stetter; Reinhold Gehring, both of Wuppertal; Otto Schallner, Monheim; Hans-Joachim Santel, Leverkusen; Robert R. Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 73,555

[22] Filed: Jul. 14, 1987

[30] Foreign Application Priority Data

Jul. 30, 1986 [DE] Fed. Rep. of Germany ....... 3625686

[51] Int. Cl.$^4$ .................... A01N 43/40; A01N 43/56; C07D 231/22; C07D 401/04
[52] U.S. Cl. ................................ 71/92; 71/86; 71/87; 546/22; 546/24; 546/279; 548/119; 548/376; 548/377
[58] Field of Search ............... 548/376, 377, 119; 71/92, 86, 87; 546/279, 22, 24

[56] References Cited

U.S. PATENT DOCUMENTS 4,459,150  7/1984  Hatton et al. .................... 71/92
4,477,462 10/1984  Aoyagi ............................ 548/376

Primary Examiner—Mary C. Lee
Assistant Examiner—Kurt G. Briscoe
Attorney, Agent, or Firm—Sprung Horn Kramer & Woods

[57] ABSTRACT

Novel herbicidal and plant-growth regulating pyrazoles of the formula

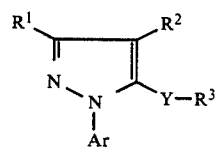

in which
  $R^1$ represents hydrogen, alkyl or halogenoalkyl,
  $R^2$ represents nitro or cyano,
  $R^3$ represents optionally substituted alkyl, optionally substituted alkenyl, optionally substituted alkinyl, optionally substituted cycloalkyl, optionally substituted cycloalkylalkyl, optionally substituted aralkyl or optionally substituted aryl,
  Ar represents phenyl which is substituted twice or more, or optionally substituted pyridyl, and
  Y represents O, S, SO or $SO_2$.

Several intermediates therefor are also new.

20 Claims, No Drawings

4-CYANO(NITRO)-5-OXY(THIO)-PYRAZOLE DERIVATIVES, COMPOSITION CONTAINING THEM, AND HERBICIDAL AND PLANT GROWTH REGULATING METHODS OF USING THEM

The invention relates to new 4-cyano(nitro)-5-oxy(thio)-pyrazole derivatives, several processes for the preparation thereof, and the use thereof as herbicides and growth regulators.

It is already known that certain 5-acylamido-1-aryl-pyrazoles, such as, for example, 4-cyano-5-propionamido-1-(2,4,6-trichlorophenyl)-pyrazole, have herbicidal properties (cf., for example, DE-OS (German Published Specification) No. 3,226,513).

However, the herbicidal activity, against weeds, of these previously known compounds and their compatibility with important crop plants are not always completely satisfactory in all areas of application.

New 4-cyano(nitro)-5-oxy(thio)-pyrazole derivatives of the formula

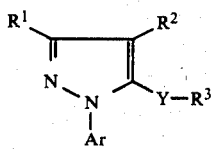
(I)

in which $R^1$ represents hydrogen, alkyl or halogenoalkyl, $R^2$ represents nitro or cyano, $R^3$ represents optionally substituted alkyl, optionally substituted alkenyl, optionally substituted alkinyl, optionally substituted cycloalkyl, optionally substituted cycloalkylalkyl, optionally substituted aralkyl or optionally substituted aryl, Ar represents phenyl which is substituted twice or more, or represents optionally substituted pyridyl, and Y represents O, S, SO or $SO_2$, have been found.

It has furthermore been found that the new 4-cyano(nitro)-5-oxy(thio)-pyrazole derivatives of the general formula (I)

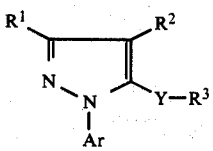
(I)

in which $R^1$ represents hydrogen, alkyl or halogenoalkyl, $R^2$ represents nitro or cyano, $R^3$ represents optionally substituted alkyl, optionally substituted alkenyl, optionally substituted alkinyl, optionally substituted cycloalkyl, optionally substituted cycloalkylalkyl, optionally substituted aralkyl or optionally substituted aryl, Ar represents phenyl which is substituted twice or more, or represents optionally substituted pyridyl, and Y represents O, S, SO or $SO_2$, are obtained with the aid of the preparation process described below.

(a) 4-Cyano(nitro)-5-oxy(thio)-pyrazole derivatives of the formula (I)

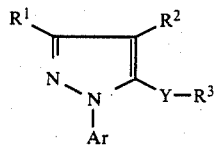
(I)

in which $R^1$, $R^2$, $R^3$, Y and Ar have the abovementioned meaning, are obtained when 5-halogeno-pyrazole derivatives of the formula (II)

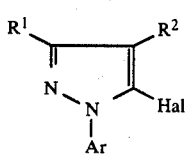
(II)

in which $R^1$, $R^2$ and Ar have the abovementioned meaning, and

Hal represents fluorine, chlorine or bromine, are reacted with nucleophilic compounds of the formula (III)

(III)

in which $R^3$ and Y have the abovementioned meaning, in the presence of a diluent and if appropriate in the presence of an acid acceptor.

(b) 4-Nitro-5-oxy(thio)-pyrazole derivatives of the formula (Ia)

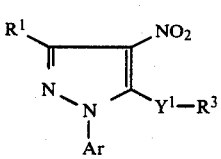
(Ia)

in which $R^1$, $R^3$ and Ar have the abovementioned meaning, and $Y^1$ represents oxygen or sulphur, are obtained when 5-oxy(thio)-pyrazole derivatives of the formula (IV)

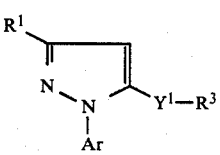
(IV)

in which $R^1$, $R^3$, $Y_1$ and Ar have the abovementioned meaning, are reacted with a nitrating agent, if appropriate in the presence of a diluent and if appropriate in the presence of a catalyst.

(c) 4-Cyano(nitro)-5-oxy(thio)-pyrazole derivatives of the formula (Ib)

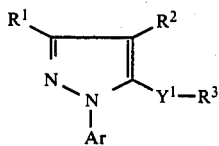

in which
R¹, R², R³, Y¹ and Ar have the abovementioned meaning, are obtained when pyrazolin-ones or pyrazoline thiones of the formula (V)

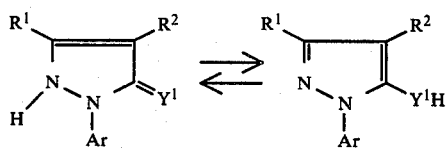

in which
R¹, R², Ar and Y₁ have the abovementioned meaning, are reacted with alkylating agents of the formula (VI)

A—R³                            (VI)

in which
R³ has the abovementioned meaning, and
A represents an electron-withdrawing leaving group, if appropriate in the presence of a diluent and if appropriate in the presence of an acid acceptor, it being possible, depending on the reaction conditions, for the corresponding N-alkylated derivatives of the formula (VII)

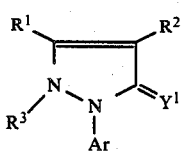

in which
R¹, R², R³, Ar and Y¹ have the abovementioned meaning, to also be obtained.

(d) 5-Sulphinyl(sulphonyl)-pyrazole derivatives of the formula (Ic)

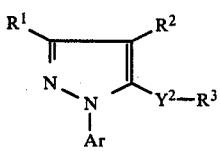

in which
R¹, R², R³ and Ar have the abovementioned meaning, and
Y² represents SO or SO₂, are obtained when 5-thiopyrazole derivatives of the formula (Id)

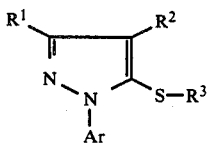

in which

R¹, R², R³ and Ar have the abovementioned meaning, are oxidized in a conventional fashion by known methods.

(e) 4-Cyano(nitro)-5-oxy(thio)-pyrazole derivatives of the formula (Ib)

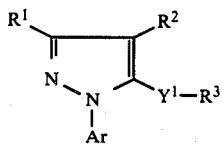

in which
R¹, R², R³, Y¹ and Ar have the abovementioned meaning, are obtained when 5-sulphonyl-pyrazole derivatives of the formula (Ie)

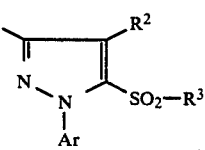

in which
R¹, R², R³ and Ar have the abovementioned meaning, are reacted with nucleophilic compounds of the formula (IIIa)

H—Y¹—R³                       (IIIa)

in which
R³ and Y¹ have the abovementioned meaning, in the presence of a diluent and if appropriate in the presence of an acid acceptor.

Finally, it has been found that the new 4-cyano(nitro)-5-oxy(thio)-pyrazole derivatives of the general formula (I) have herbicidal, particularly also selective herbicidal, and also growth-regulating properties.

Surprisingly, the 4-cyano(nitro)-5-oxy(thio)-pyrazole derivatives of the general formula (I) according to the invention exhibit a considerably better general herbicidal activity against problem weeds which are difficult to combat and simultaneously a markedly improved compatibility with important crop plants compared to the 5-acylamido-1-aryl-pyrazoles which are known from the state of the art, such as, for example, 4-cyano-5-propionamido-1-(2,4,6-trichlorophenyl)-pyrazole, which are similar compounds chemically and regarding their action.

The 4-cyano(nitro)-5-oxy(thio)-pyrazole derivatives according to the invention are generally defined by the formula (I). Preferred compounds of the formula (I) are those in which
R¹ represents hydrogen, straight-chain or branched alkyl having 1 to 4 carbon atoms, or straight-chain or branched halogenoalkyl having 1 to 4 carbon atoms and 1 to 9 identical or different halogen atoms,
R² represents nitro or cyano,
R³ represents in each case optionally substituted, straight-chain or branched alkyl, alkenyl and alkinyl in each case having up to 6 carbon atoms, where the following may be mentioned in each case as substituents: halogen; alkoxy, alkylthio, alkylsulphinyl, alkylsulphonyl and dialkoxy in each case having 1 to 4 carbon atoms in the alkyl parts; cyano; hydroxycarbonyl; alkoxycarbonyl, alkylthiocarbonyl and alkylcarbonyl in each case having 1 to 4 carbon atoms in the alkyl part; aminocarbonyl; alkylaminocarbonyl and dialkylaminocarbonyl in each case having 1 to 4 carbon atoms in the alkyl parts; hydroxyimino and alkoximino having 1 to 4 carbon atoms; and the

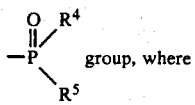 group, where $R^4$ and $R^5$ are identical or different and represent hydroxyl, alkyl and alkoxy in each case having 1 to 4 carbon atoms, and also phenyl and phenoxy which are in each case optionally mono- or poly-substituted, where the substituents are identical or different and where the radicals which are suitable as phenyl substituents for Ar are preferably mentioned as substituents; furthermore represents cycloalkyl and cycloalkylalkyl, having 3 to 7 carbon atoms in the cycloalkyl part and 1 to 2 carbon atoms in the alkyl part, which are in each case optionally mono- or polysubstituted, where the substituents are identical or different and where the following may be mentioned in each case as substituents in the cycloalkyl part: halogen, alkyl, alkoxy and alkylthio in each case having 1 to 4 carbon atoms; or represents phenyl and phenylalkyl, having 1 to 4 carbon atoms in the straight-chain or branched alkyl part, which are in each case optionally mono- or polysubstituted, where the substituents are identical or different and suitable phenyl substituents in each case being: halogen, cyano, nitro, in each case straight-chain or branched alkyl, alkoxy, alkylthio, alkylsulphinyl, alkylsulphonyl, halogenoalkyl, halogenoalkoxy, halogenoalkylthio, halogenoalkylsulphinyl or halogenoalkylsulphonyl in each case having 1 to 4 carbon atoms in the individual alkyl parts and, if appropriate, 1 to 9 identical or different halogen atoms;

Y represents O, S, SO or $SO_2$, and

Ar represents phenyl which is substituted twice or more, and 2-pyridyl, 3-pyridyl or 4-pyridyl which are in each case optionally mono- or polysubstituted, where the substituents are identical or different and where the following are suitable as phenyl or pyridyl substituents: cyano, nitro, halogen, in each case straight-chain or branched alkyl, alkoxy or alkoxycarbonyl in each case having up to 4 carbon atoms, in addition in each case straight-chain or branched halogenoalkyl or halogenoalkoxy in each case having up to 4 carbon atoms and up to 9 identical or different halogen atoms, or a $—S(O)_mR^6$ radical where $R^6$ represents amino, and also in each case straight-chain or branched alkyl, alkylamino, dialkylamino or halogenoalkyl in each case having up to 4 carbon atoms in the individual alkyl parts and, in the case of halogenoalkyl, having up to 9 identical or different halogen atoms, and m represents a number 0, 1 or 2.

Particularly preferred compounds of the formula (I) are those in which $R^1$ represents hydrogen, methyl, ethyl, n- or i-propyl and trifluoromethyl;

$R^2$ represents nitro or cyano;

$R^3$ represents methyl, ethyl; n- or i-propyl; n-, i-, s- or t-butyl; n- or i-pentyl; n- or i-hexyl, allyl, propenyl, butenyl, propargyl or butinyl, which may in each case be mono- or polysubstituted by fluorine, chlorine, bromine, methoxy, ethoxy, methylthio, ethylthio, methylsulphinyl, methylsulphonyl, dimethoxy, diethoxy, cyano, hydroxycarbonyl, methoxycarbonyl, ethoxycarbonyl, propoxycarbonyl, butoxycarbonyl, aminocarbonyl, methylaminocarbonyl, dimethylaminocarbonyl, methylthiocarbonyl, methylcarbonyl, hydroximino, methoxyimino, ethoximino, phosphonyl, methylphosphinoyl, dimethylphosphinoyl, methyl-ethyl-phosphinoyl, dimethylphosphonoyl and diethylphosphonoyl, the substituents being identical or different; furthermore represents cyclopropyl, cyclopentyl, cyclohexyl, cyclopropylmethyl, cyclopentylmethyl or cyclohexylmethyl which may in each case be mono- or disubstituted by fluorine, chlorine or methyl, the substituents being identical or different; or represents phenyl, benzyl or phenylethyl which are in each case optionally mono- or trisubstituted and suitable phenyl substituents being: fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl and trifluoromethylsulphonyl;

Y represents O, S, SO or $SO_2$, and

Ar represents phenyl which is substituted twice or more, and also 2-pyridyl, 3-pyridyl or 4-pyridyl which are in each case optionally mono- or tetrasubstituted, the substituents being identical or different and suitable phenyl or pyridyl substituents being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, dichlorofluoromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an $—S(O)_mR^6$ radical, where $R^6$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, and m represents a number 0, 1 or 2.

Compounds of the formula (I) which should be particularly emphasized are those in which Y represents oxygen or sulphur, and $R^1$, $R^2$, $R^3$ and Ar have the meaning mentioned above as being particularly preferred.

Apart from the compounds mentioned in the preparation examples, the 4-cyano(nitro)-5-oxy(thio)-pyrazole derivatives of the general formula (I) listed by their formulae in the following table may be mentioned individually:

TABLE 1

(I)

structure: pyrazole with R¹, R² on ring, N-N, Y-R³, N-Ar

| R¹ | R² | R³ | Y | Ar |
|---|---|---|---|---|
| H | NO₂ | —CH₂—COOH | O | 2-Cl-4-CF₃-phenyl |
| H | NO₂ | —CH₂—COOCH₃ | O | 2-Cl-4-CF₃-phenyl |
| H | NO₂ | —CH₂—COOC₂H₅ | O | 2-Cl-4-CF₃-phenyl |
| H | NO₂ | —CH₂CN | O | 2-Cl-4-CF₃-phenyl |
| H | NO₂ | —CH₂—P(=O)(OCH₃)(OCH₃) | O | 2-Cl-4-CF₃-phenyl |
| H | NO₂ | —CH₂—C(=O)—NH₂ | O | 2-Cl-4-CF₃-phenyl |
| H | NO₂ | —CH₂—C(=O)—N(CH₃)₂ | O | 2-Cl-4-CF₃-phenyl |
| H | NO₂ | —CH₂—CH=CH₂ | O | 2-Cl-4-CF₃-phenyl |
| H | NO₂ | —CH₂—C≡CH | O | 2-Cl-4-CF₃-phenyl |
| H | NO₂ | —CH₂CH₂CN | O | 2-Cl-4-CF₃-phenyl |
| H | NO₂ | —CH₂CH₂C(=O)—OCH₃ | O | 2-Cl-4-CF₃-phenyl |
| H | NO₂ | —CH₂CH₂OCH₃ | O | 2-Cl-4-CF₃-phenyl |
| H | NO₂ | —CH₂—phenyl | O | 2-Cl-4-CF₃-phenyl |
| H | NO₂ | —CH₂—CH=N—OCH₃ | O | 2-Cl-4-CF₃-phenyl |
| H | NO₂ | —CH₂—C(CH₃)=N—OCH₃ | O | 2-Cl-4-CF₃-phenyl |
| H | CN | —C₂H₅ | O | 2-Cl-4-CF₃-phenyl |
| H | CN | —C₃H₇ | O | 2-Cl-4-CF₃-phenyl |
| H | CN | —CH(CH₃)—COOC₄H₉ | O | 2-Cl-4-CF₃-phenyl |
| H | CN | —CH₂CN | O | 2-Cl-4-CF₃-phenyl |
| H | CN | —CH₂—COOCH₃ | O | 2-Cl-4-CF₃-phenyl |

TABLE 1-continued

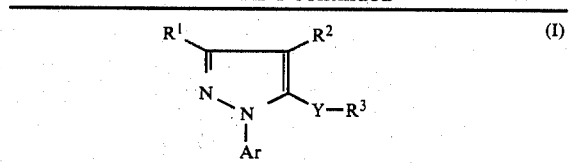

| R¹ | R² | R³ | Y | Ar |
|---|---|---|---|---|
| H | CN | —CH₂—CONH₂ | O | 2-Cl, 4-CF₃-phenyl |
| H | CN | —CH₂—CO—N(CH₃)₂ | O | 2-Cl, 4-CF₃-phenyl |
| H | CN | —CH(CH₃)—CO—NH₂ | O | 2-Cl, 4-CF₃-phenyl |
| H | CN | —CH(CH₃)—CO—N(CH₃)₂ | O | 2-Cl, 4-CF₃-phenyl |
| H | CN | —CH₂—P(=O)(OCH₃)₂ | O | 2-Cl, 4-CF₃-phenyl |
| H | CN | —CH₂—P(=O)(OC₂H₅)₂ | O | 2-Cl, 4-CF₃-phenyl |
| H | NO₂ | —CH₂—COOCH₃ | O | 2,6-Cl₂, 4-CF₃-phenyl |
| H | NO₂ | —CH₂—COOC₄H₉ | O | 2,6-Cl₂, 4-CF₃-phenyl |
| H | NO₂ | —CH(CH₃)—CO—NH₂ | O | 2,6-Cl₂, 4-CF₃-phenyl |
| H | NO₂ | —CH(CH₃)—COOH | O | 2,6-Cl₂, 4-CF₃-phenyl |
| H | NO₂ | —CH(CH₃)—CO—N(CH₃)₂ | O | 2,6-Cl₂, 4-CF₃-phenyl |
| H | NO₂ | —CH₂CN | O | 2,6-Cl₂, 4-CF₃-phenyl |
| H | NO₂ | —CH₂—P(=O)(OCH₃)₂ | O | 2,6-Cl₂, 4-CF₃-phenyl |
| H | NO₂ | —CH₂—P(=O)(OC₂H₅)₂ | O | 2,6-Cl₂, 4-CF₃-phenyl |
| H | NO₂ | —CH(CH₃)—P(=O)(OCH₃)₂ | O | 2,6-Cl₂, 4-CF₃-phenyl |
| H | NO₂ | —CH(CH₃)—P(=O)(OC₂H₅)₂ | O | 2,6-Cl₂, 4-CF₃-phenyl |
| H | NO₂ | —CH₂CH₂—COOCH₃ | O | 2,6-Cl₂, 4-CF₃-phenyl |

TABLE 1-continued

Structure (I): Pyrazole with R¹ at 3-position, R² at 4-position, Y-R³ at 5-position, Ar at N1.

| R¹ | R² | R³ | Y | Ar |
|---|---|---|---|---|
| H | NO₂ | —CH₂CH₂CN | O | 2,6-Cl₂-4-CF₃-C₆H₂ |
| H | NO₂ | —CH₂—C≡CH | O | 2,6-Cl₂-4-CF₃-C₆H₂ |
| H | NO₂ | —CH₂—CH=N—OCH₃ | O | 2,6-Cl₂-4-CF₃-C₆H₂ |
| H | NO₂ | —CH₂—C(CH₃)=N—OCH₃ | O | 2,6-Cl₂-4-CF₃-C₆H₂ |
| H | NO₂ | —CH₂CH₂OCH₃ | O | 2,6-Cl₂-4-CF₃-C₆H₂ |
| H | CN | —CH₂—COOCH₃ | O | 2,6-Cl₂-4-CF₃-C₆H₂ |
| H | CN | —CH₂—C(O)—NH₂ | O | 2,6-Cl₂-4-CF₃-C₆H₂ |
| H | CN | —CH₂—C(O)—N(CH₃)₂ | O | 2,6-Cl₂-4-CF₃-C₆H₂ |
| H | CN | —CH(CH₃)—COOCH₃ | O | 2,6-Cl₂-4-CF₃-C₆H₂ |
| H | CN | —CH(CH₃)—COOC₂H₅ | O | 2,6-Cl₂-4-CF₃-C₆H₂ |
| H | CN | —CH(CH₃)—CO—NH₂ | O | 2,6-Cl₂-4-CF₃-C₆H₂ |
| H | CN | —CH(CH₃)—CO—N(CH₃)₂ | O | 2,6-Cl₂-4-CF₃-C₆H₂ |
| H | CN | —CH₂CH₂OCH₃ | O | 2,6-Cl₂-4-CF₃-C₆H₂ |
| H | CN | —CH₂CH₂COOCH₃ | O | 2,6-Cl₂-4-CF₃-C₆H₂ |
| H | CN | —CH₂—CH₂COOC₄H₉ | O | 2,6-Cl₂-4-CF₃-C₆H₂ |
| H | NO₂ | —CH₂—COOCH₃ | O | 2,3-Cl₂-5-CF₃-C₆H₂ |

TABLE 1-continued

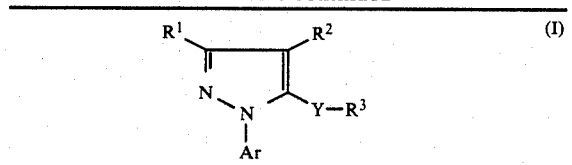

(I)

| R¹ | R² | R³ | Y | Ar |
|---|---|---|---|---|
| H | NO$_2$ | -CH(CH$_3$)-COOCH$_3$ | O | 2,6-dichloro-4-(trifluoromethyl)phenyl |
| H | NO$_2$ | -CH$_2$COOC$_2$H$_5$ | O | 2,6-dichloro-4-(trifluoromethyl)phenyl |
| H | NO$_2$ | -CH(CH$_3$)-COOC$_2$H$_5$ | O | 2,6-dichloro-4-(trifluoromethyl)phenyl |
| H | NO$_2$ | -CH$_2$-COOC$_4$H$_9$ | O | 2,6-dichloro-4-(trifluoromethyl)phenyl |
| H | NO$_2$ | -CH$_2$-COOH | O | 2,6-dichloro-4-(trifluoromethyl)phenyl |
| H | NO$_2$ | -CH(CH$_3$)-COOH | O | 2,6-dichloro-4-(trifluoromethyl)phenyl |
| H | NO$_2$ | -CH$_2$-P(=O)(OCH$_3$)$_2$ | O | 2,6-dichloro-4-(trifluoromethyl)phenyl |
| H | NO$_2$ | -CH$_2$-P(=O)(OC$_2$H$_5$)$_2$ | O | 2,6-dichloro-4-(trifluoromethyl)phenyl |
| H | NO$_2$ | -CH$_2$CN | O | 2,6-dichloro-4-(trifluoromethyl)phenyl |
| H | NO$_2$ | -CH$_2$CH$_2$OCH$_3$ | O | 2,6-dichloro-4-(trifluoromethyl)phenyl |
| H | NO$_2$ | -CH$_3$ | O | 2,6-dichloro-4-(trifluoromethyl)phenyl |
| H | NO$_2$ | -C$_2$H$_5$ | O | 2,6-dichloro-4-(trifluoromethyl)phenyl |
| H | NO$_2$ | -C$_3$H$_7$ | O | 2,6-dichloro-4-(trifluoromethyl)phenyl |
| H | NO$_2$ | -CH$_2$CH=CH$_2$ | O | 2,6-dichloro-4-(trifluoromethyl)phenyl |
| H | NO$_2$ | -CH$_2$-CH=N-OCH$_3$ | O | 2,6-dichloro-4-(trifluoromethyl)phenyl |
| H | CN | -CH$_2$-COOCH$_3$ | O | 2,6-dichloro-4-(trifluoromethyl)phenyl |

TABLE 1-continued

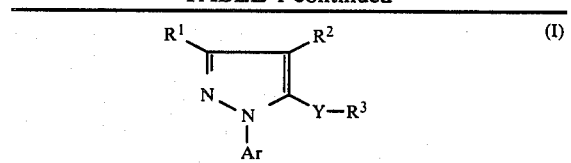

| R¹ | R² | R³ | Y | Ar |
|---|---|---|---|---|
| H | CN | -CH(CH₃)-COOCH₃ | O | 2,6-Cl₂-4-CF₃-phenyl |
| H | CN | -CH₂-COOC₂H₅ | O | 2,6-Cl₂-4-CF₃-phenyl |
| H | CN | -CH(CH₃)-COOC₂H₅ | O | 2,6-Cl₂-4-CF₃-phenyl |
| H | CN | -CH₂-COOH | O | 2,6-Cl₂-4-CF₃-phenyl |
| H | CN | -CH(CH₃)-COOH | O | 2,6-Cl₂-4-CF₃-phenyl |
| H | CN | -CH₂-P(=O)(OC₂H₅)₂ | O | 2,6-Cl₂-4-CF₃-phenyl |
| H | CN | -CH₃ | O | 2,6-Cl₂-4-CF₃-phenyl |
| H | CN | -C₂H₅ | O | 2,6-Cl₂-4-CF₃-phenyl |
| H | CN | -CH₂CN | O | 2,6-Cl₂-4-CF₃-phenyl |
| H | NO₂ | -CH₃ | O | 2,3,5,6-F₄-4-CF₃-phenyl |
| H | NO₂ | -C₂H₅ | O | 2,3,5,6-F₄-4-CF₃-phenyl |
| H | NO₂ | -CH₂-COOH | O | 2,3,5,6-F₄-4-CF₃-phenyl |
| H | NO₂ | -CH₂-COOCH₃ | O | 2,3,5,6-F₄-4-CF₃-phenyl |
| H | NO₂ | -CH(CH₃)-COOH | O | 2,3,5,6-F₄-4-CF₃-phenyl |
| H | NO₂ | -CH(CH₃)-COOC₄H₉ | O | 2,3,5,6-F₄-4-CF₃-phenyl |
| H | NO₂ | -CH(CH₃)-COOCH₃ | O | 2,3,5,6-F₄-4-CF₃-phenyl |

TABLE 1-continued

Structure (I): Pyrazole with R¹ at 3-position, R² at 4-position, Y-R³ at 5-position, Ar at N1.

| R¹ | R² | R³ | Y | Ar |
|---|---|---|---|---|
| H | NO₂ | —CH₂CN | O | 2,3,5,6-tetrafluoro-4-CF₃-phenyl |
| H | NO₂ | —CH₂—P(=O)(OC₂H₅)(OC₂H₅) | O | 2,3,5,6-tetrafluoro-4-CF₃-phenyl |
| H | NO₂ | —CH₂—CH=CH₂ | O | 2,3,5,6-tetrafluoro-4-CF₃-phenyl |
| H | NO₂ | —CH₂—C≡CH | O | 2,3,5,6-tetrafluoro-4-CF₃-phenyl |
| H | CN | —CH₃ | O | 2,3,5,6-tetrafluoro-4-CF₃-phenyl |
| H | CN | —C₂H₅ | O | 2,3,5,6-tetrafluoro-4-CF₃-phenyl |
| H | CN | —CH₂—COOH | O | 2,3,5,6-tetrafluoro-4-CF₃-phenyl |
| H | CN | —CH(CH₃)—COOCH₃ | O | 2,3,5,6-tetrafluoro-4-CF₃-phenyl |
| H | CN | —CH(CH₃)—COOC₂H₅ | O | 2,3,5,6-tetrafluoro-4-CF₃-phenyl |
| H | CN | —CH(CH₃)—COOC₄H₉ | O | 2,3,5,6-tetrafluoro-4-CF₃-phenyl |
| H | CN | —CH₂—COOCH₃ | O | 2,3,5,6-tetrafluoro-4-CF₃-phenyl |

If, for example, 5-chloro-1-(2,6-dichloro-4-trifluoromethyl-phenyl)-4-nitro-pyrazole and propanol are used as starting materials, then the course of the reaction of the process (a) according to the invention may be represented by the following equation:

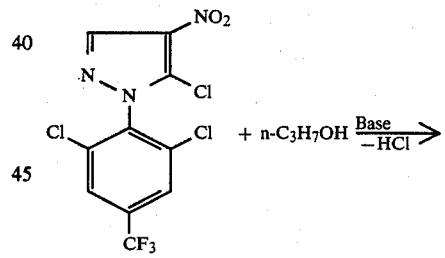

If, for example 1-(2-chloro-4-trifluoromethoxyphenyl)-3-methyl-5-methoxycarbonylmethoxypyrazole and nitric acid are used as starting materials, then the course of the reaction of the process (b) according to the invention may be represented by the following equation:

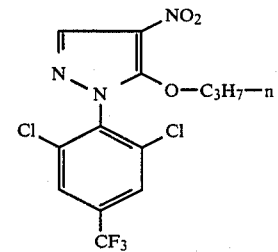

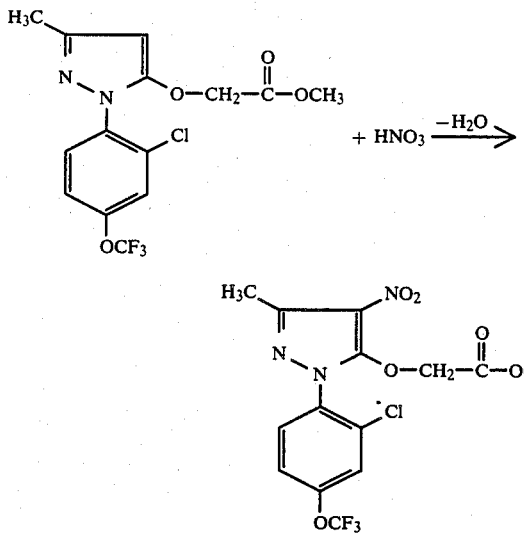

If, for example, 4-cyano-1-(2,4-dichloro-phenyl)-pyrazoline 5-thione and methyl iodide are used as starting materials, then the course of the reaction of the process (c) according to the invention may be represented by the following equation:

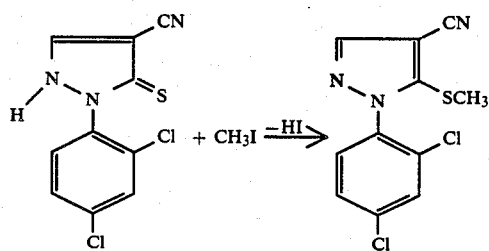

If, for example, 1-(2-bromo-4-trifluoromethyl-phenyl)-5-methylthio-4-nitro-pyrazole and hydrogen peroxide are used as starting materials, then the course of the reaction of the process (d) according to the invention may be represented by the following equation:

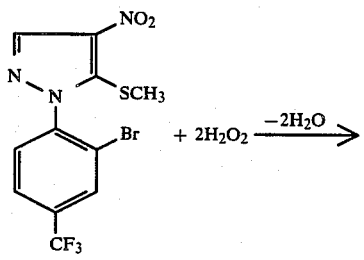

If, for example, 4-cyano-5-methylsulphonyl-1-(2,4,6-trichloro-phenyl)-pyrazole and N,N-dimethyl-hydroxyacetamide are used as starting materials, then the course of the reaction of the process (e) according to the invention may be represented by the following equation:

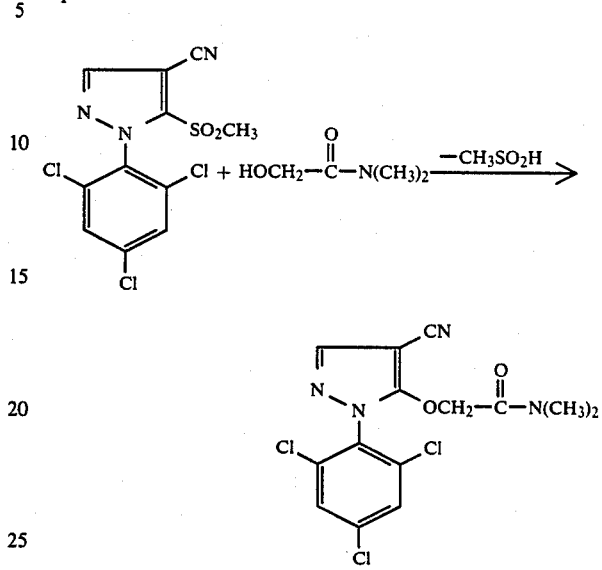

Formula (II) provides a general definition of the 5-halogenopyrazole derivatives required as starting materials for carrying out the process (a) according to the invention. In this formula, $R^1$, $R^2$ and Ar preferably represent those meanings which have already been mentioned in connection with the description of the substances of the formula (I) according to the invention as being preferred for these substituents.

5-Halogeno-pyrazole derivatives of the formula (II) are the subject matter of U.S. Ser. No. 866,050 filed May 22, 1986 now pending, U.S. Ser. No. 815,440 filed Dec. 31, 1985 now pending and U.S. Ser. No. 885,051 filed July 14, 1986 now U.S. Pat. No. 4,685,956, and can be obtained according to the process described there by, for example, reacting 5-amino-pyrazoles of the general formula (VIII)

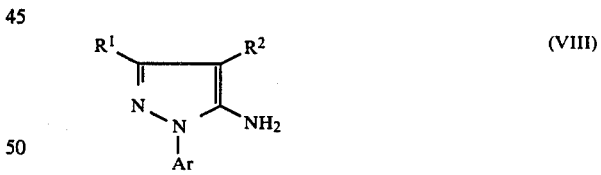

in which $R^1$, $R^2$ and Ar have the abovementioned meaning, either with nitrile compounds of the formula (IX)

$$R^7-O-N=O \qquad (IX)$$

in which $R^7$ represents hydrogen, an alkali metal cation or alkyl, and with a haloform of the formula (X)

in which

Hal has the abovementioned meaning, or with sodium nitrite in the presence of a hydrohalic acid of the formula (XI)

H—Hal (XI)

in which

Hal has the abovementioned meaning, in each case if appropriate in the presence of a diluent, such as, for example, excess haloform or excess hydrohalic acid, and if appropriate in the presence of a catalyst, such as, for example, an acid, at temperatures between −20° and +120° C.; or by reacting halogeno-pyrazoles of the general formula (XII)

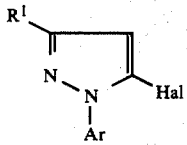
(XII)

in which $R^1$, Ar and Hal have the abovementioned meaning, with a nitrating agent, such as, for example, nitric acid, corresponding to the information for process version (b).

The 5-amino-pyrazoles of the formula (VIII) are known (See U.S. Ser. No. 659,731 filed Oct. 11, 1984 now U.S. Pat. No. 4,668,280 and U.S. Pat. No. 4,614,533 issued Sept. 30, 1986) or can be obtained by the processes described there.

The nitrite compounds of the formula (IX), the haloforms of the formula (X) and the hydrohalic acids of the formula (XI) are generally known compounds of organic chemistry.

The halogeno-pyrazoles of the formula (XII) were hitherto not known. They can be obtained by reacting alkoxymethylenemalonate of the formula (XIII)

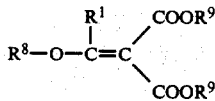
(XIII)

in which $R^1$ has the abovementioned meaning, and $R^8$ and $R^9$, independently of one another, represent alkyl, preferably methyl or ethyl, initially in a first stage, with arylhydrazines of the formula (XIV)

Ar—NHNH$_2$ (XIV)

in which

Ar has the abovementioned meaning, if appropriate in the presence of diluent, such as, for example, methanol or ethanol, at temperatures between 10° C. and 80° C., (The intermediate of the formula (XIVa)

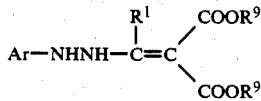
(XIVa)

in which $R^1$, $R^9$ and Ar have the abovementioned meaning, can, if appropriate, also be isolated and cyclized in a separate reaction stage) and decarboxylating the pyrazolecarboxylates thus obtainable of the formula (XV)

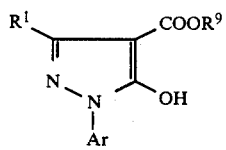
(XV)

in which $R^1$, $R^9$ and Ar have the abovementioned meaning, in a second stage, if appropriate in the presence of a diluent, such as, for example, methanol, and if appropriate in the presence of a base, such as, for example, sodium hydroxide, at temperatures between 30° C. and 70° C.

The cyclization and subsequent decarboxylation may, if appropriate, alternatively be carried out in one reaction stage as a 'one-pot process' (cf., for example, Liebigs Ann. Chem. 373, 142 (1910), and the preparation examples).

The pyrazolinones of the formula (XVIa)

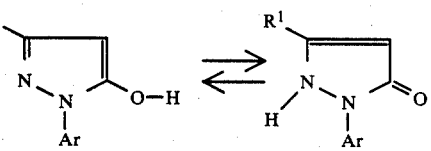
(XVIa)

in which $R^1$ and Ar have the abovementioned meaning, thus obtained are reacted, in a third stage, with halogenating agents, such as, for example, phosphoryl chloride or phosphoryl bromide, according to conventional, known processes (cf., for example, Ber. dtsch. Chem. Gesellschaft 28, 35 (1895) or Liebigs Ann. Chem. 373, 129 (1910)).

The alkoxymethylenemalonates of the formula (XIII) are generally known compounds of organic chemistry.

The arylthydrazines of the formula (XIV) are known or can be obtained by known processes (cf., for example, Houben-Weyl, Methoden der organischen Chemie [Methods of Organic Chemistry], volume X, 2; page 203, Thieme Verlag Stuttgart 1967).

The pyrazolinones of the formula (XVI) can also be obtained by reacting β-keto esters of the formula (XVII)

$R^1$—CO—CH$_2$—COOR$^9$ (XVII)

in which $R^1$ and $R^9$ have the abovementioned meaning, with arylhydrazines of the formula (XIV), if appropriate in the presence of a diluent, such as, for example, toluene, and if appropriate in the presence of a catalyst, such as, for example, p-toluenesulphonic acid, at temperatures between 0° C. and 120° C. (cf. also the preparation examples).

Formula (III) provides a general definition of the nucleophilic compounds which are additionally required as starting materials for carrying out the process (a) according to the invention. In this formula, $R^3$ and Y preferably represent those meanings which have already been mentioned in connection with the description of the substances of the formula (I) according to the invention as being preferred for these substituents.

The nucleophilic compounds of the formula (III) are generally known compounds of organic chemistry.

Formula (IV) provides a general definition of the 5-oxy(thio)-pyrazole derivatives which are required as starting materials for carrying out the process (b) according to the invention. In this formula, $R^1$, $R^3$ and Ar preferably represent those meanings which have already been mentioned in connection with the description of the substances of the formula (I) according to the invention as being preferred for these substituents. $Y^1$ preferably represents oxygen or sulphur.

The 5-oxy(thio)-pyrazole derivatives of the formula (IV) were hitherto not known. They can be obtained by reacting pyrazolin-ones or pyrazoline thiones of the formula (XVI)

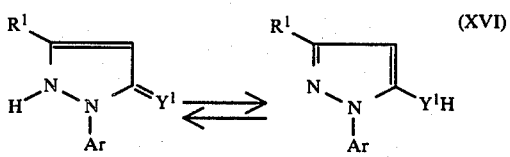

in which $R^1$, Ar and $Y^1$ have the abovementioned meaning, with alkylating agents of the formula (VI) according to the information of process (c) according to the invention.

The pyrazolin-ones of the formula (XVIa)

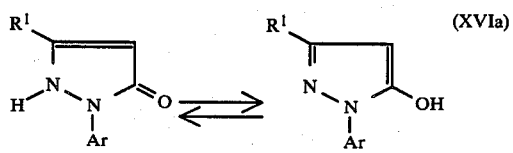

in which $R^1$ and Ar have the abovementioned meaning, can be obtained correspondingly to the above information of the process (a) according to the invention.

The pyrazoline thiones of the formula (XVIb)

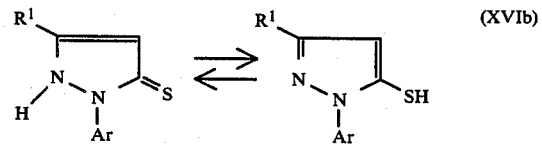

in which $R^1$ and Ar have the abovementioned meaning, can be obtained by reacting the pyrazolin-ones of the formula (XVIa) with conventional sulphur reagents, such as, for example, phosphorus pentasulphide, in a generally conventional and known fashion.

Formula (V) provides a general definition of the pyrazolin-ones and pyrazoline thiones which are required as starting materials for carrying out the process (c) according to the invention. In this formula, $R^1$, $R^2$ and Ar preferably represent those meanings which have already been mentioned in connection with the description of the substances of the formula (I) according to the invention as being preferred for these substituents. $Y^1$ preferably represents oxygen or sulphur.

The pyrazolin-ones and pyrazoline thiones of the formula (V) were hiterto not known. They can be obtained, for example, by reacting pyrazolin-ones of the formula (XVIa) or pyrazoline thiones of the formula (XVIb) with a nitrating agent, such as, for example, nitric acid, according to the information of process (b) according to the invention; or by hydrolyzing 5-halogeno-pyrazole derivatives of the formula (II) in a generally conventional fashion using water or using aqueous alkali metal or alkaline earth metal bases, or thiolyzing them using hydrogen sulphide or using alkali metal or alkaline earth metal salts of hydrogen sulphide.

Formula (VI) provides a general definition of the alkylating agents which are additionally required as starting materials for carrying out the process (c) according to the invention. In this formula, $R^3$ preferably represents those meanings which have already been mentioned in connection with the description of the substances of the formula (I) according to the invention as being preferred for these substituents. A preferably represents chlorine, bromine, iodine, p-toluenesulphonyloxy or methoxysulphonyloxy.

The alkylating agents of the formula (VI) are generally known compounds of organic chemistry.

The 5-thiopyrazole derivatives of the formula (Id) which are required as starting materials for carrying out the process (d) according to the invention are compounds according to the invention and can be obtained corresponding to the processes (a), (b) or (c) according to the invention.

The oxidation according to the process (d) according to the invention is carried out by reaction with conventional inorganic and organic oxidants.

These preferably include organic peracids, such as, for example, peracetic acid, p-nitroperbenzoic acid, m-chloroperbenzoic acid; inorganic peracids, such as, for example, periodic acid; furthermore hydrogen peroxide in glacial acetic acid or methanol, potassium permanganate or chromic acid.

The 5-sulphonyl-pyrazole derivatives of the formula (Ie) which are required as starting materials for carrying out the process (e) according to the invention are compounds according to the invention and can be obtained corresponding to the processes (a) or (d) according to the invention.

Formula (IIIa) provides a general definition of the nucleophilic compounds which are additionally required as starting materials for carrying out the process (e) according to the invention. In this formula, $R^3$ preferably represents those meanings which have already been mentioned in connection with the description of the substances of the formula (I) according to the invention as being preferred for this substituent. $Y^1$ preferably represents oxygen or sulphur.

The nucleophilic compounds of the formula (IIIa) are generally known compounds of organic chemistry.

Suitable diluents for carrying out the preparation processes (a), (c) and (e) are inert organic solvents. These include, in particular, aliphatic and aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, alcohols, such as methanol, ethanol or isopropanol, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide. In some cases, it proves advantageous to work in aqueous-organic homogeneous or two-phase systems (phase transfer catalysis).

In a particular embodiment of the processes (a), (c) and (e), the alkali metal salts or alkaline earth metal salts of the nucleophilic compounds of the formula (III) or of the pyrazolin-ones or pyrazoline thiones of the formula (V) are employed as reactants.

The preparation processes (a), (c) and (e) are, if appropriate, carried out in the presence of an acid acceptor.

Suitable as such are all conventional inorganic or organic bases. These include, for example, alkali metal hydroxides, such as sodium hydroxide or potassium hydroxide, alkali metal carbonates, such as sodium carbonate, potassium carbonate or sodium hydrogen carbonate, alkali metal hydrides, such as sodium hydride, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures may be varied within a relatively wide range in the processes (a) and (e) according to the invention. In general, the processes are carried out at temperatures between $-20°$ C. °C. and $+120°$ C, preferably at temperatures between $-10°$ C. and $+80°$ C.

The reaction temperatures may be varied within a relatively wide range in the process (c) according to the invention. In general, the process is carried out at temperatures between $-20°$ C. and $+80°$ C., preferably at temperatures between $0°$ C. and $+50°$ C.

To carry out the preparation process (a), 1 to 10 mols, preferably 1 to 5 mols, of the nucleophilic compound of the formula (III) and, if appropriate, 1 to 5 mols of acid acceptor are generally employed per mol of 5-halogeno-pyrazole derivative of the formula (II). The reaction is controlled and the reaction products are worked up and isolated by generally known and conventional processes.

To carry out the preparation process (c), 1 to 10 mols, preferably 1 to 5 mols, of the alkylating agent of the formula (VI) and 1 to 5 mol of acid acceptor are generally employed per mol of the pyrazolin-ones or pyrazoline thiones of the formula (V). The reaction is controlled and the reaction products are worked up and isolated by generally known and conventional processes.

To carry out the preparation process (e), 1 to 10 mols, preferably 1 to 5 mols, of the nucleophilic compound of the formula (IIIa) and, if appropriate, 1 to 5 mols of acid acceptor are generally employed per mol of the 5-sulphonyl-pyrazole derivative of the formula (Ie). The reaction is controlled and the reaction products are worked up and isolated by generally known and conventional processes.

Nitric acid and nitrating acid are preferably suitable as nitrating agents for carrying out the preparation process (b).

All solvents which can conventionally be used for such nitration reactions are suitable as diluents for carrying out the process (b) according to the invention. The acids which are suitable as reagents, or the mixtures thereof with catalyst acids, such as, for example, sulphuric acid, nitric acid, acetic anhydride or nitrating acid, are preferably simultaneously used as diluents.

Inert organic solvents, such as, for example, glacial acetic acid or chlorinated hydrocarbons, such as methylene chloride, chloroform or carbon tetrachloride, are, if appropriate, also suitable as diluent.

The catalysts which are conventional for such nitrations are likewise suitable as catalysts for carrying out the process (b) according to the invention; acid catalysts, such as, for example, sulphuric acid or acetic anhydride, are preferably used.

The reaction temperatures may be varied within a relatively wide range when carrying out the process (b) according to the invention. In general, the process is carried out between $-50°$ C. and $+200°$ C., preferably between $-20°$ C. and $+150°$ C.

To carry out the process (b) according to the invention, 1.0 to 100 mols, preferably 1.0 to 50 mols, of nitric acid and, if appropriate, 0.1 to 10 mols of catalyst are generally employed per mol of 5-oxy(thio)pyrazole derivative of the formula (IV).

The reaction is controlled and the reaction products are worked up and isolated in a generally conventional fashion.

The reaction temperatures may be varied within a relatively wide range when carrying out the oxidation according to the preparation process (d). In general, the process is carried out between $-50°$ C. and $100°$ C., preferably between $-30°$ C. and $80°$ C.

When carrying out the oxidation according to the invention according to preparation process (d), about 1 to 5 moles of oxidant are employed per mole of 5-thiopyrazole derivatives of the formula (Id). When 1 mole of oxidant, such as m-chloroperbenzoic acid in methylene chloride or hydrogen peroxide in acetic anhydride, is used at temperatures between $-30°$ C. to $+30°$ C., the compounds of the formula (Ic) according to the invention are preferably produced with an SO group. With an excess of oxidant and elevated temperatures ($10°$ to $80°$ C.), the compounds of the formula (Ic) according to the invention are preferably produced with an $SO_2$ group. The oxidation products are isolated in a conventional fashion.

The active compounds according to the invention can be used as defoliants, desiccants, agents for destroying broad-leaved plants and, especially, as weedkillers. By weeds, in the broadest sense, there are to be understood all plants which grown in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success for selectively combating monocotyledon and dicotyledon weeds, in monocotyledon and dicotyledon cultures, such as cotton, wheat, maize and barley, in the pre-emergent and post-emergent method.

In addition to this, the active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, dusting agents, foams, pastes, soluble powders, granules, suspension emulsion concentrates, natural and synthetic materials impregnated with active compound, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders of carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut sheels, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans. Mixing with N,N-dimethyl-N'-(3-trifluoromethyl-phenyl)-urea; N,N-dimethyl-N'-(3-chloro-4-methylphenyl)-urea; N,N-dimethyl-N'-(4-isopropylphenyl)-urea; 4-amino-6-t-butyl-3-ethylthio-1,2,4-triazin-5(4H)-one; 2,4-di-chlorophenoxyacetic acid; (2-methyl-4-chloro-phenoxy)-acetic acid; (4-chloro-2-methylphenoxy)-propionic acid; 2,6-diethyl-N-(methoxymethyl)-chloroacetanilide; 2-ethyl-6-methyl-N-(1-methyl-2- methoxyethyl)-chloroacetanilide; trimethylsilylmethyl 2-[4-(3,5-dichloropyrid-2-yl-oxy)-phenoxy]-propionate; methyl 5-(2,4-dichlorophenoxy)-2-nitrobenzoate; 3,5-diiodo-4-hydroxybenzonitrile; 3-isopropyl-2,1,3-benzodiazin-4-one 2,2-dioxide; 2-chloro-N-}[(4-methoxy-6-methyl-1,3,5-triazin-2-yl)-amino]-carbonyl}-benzenesulphonamide; 4-ethylamino-2-t-butylamino-6-methyl-thio-s-triazine; N-methyl-2-(1,3-benzthiazol-2-yloxy)-acetanilide; S-ethyl N,N-di-n-propyl-thiocarbamate; exo-1-methyl-4-(1-methylethyl)-2-(2-methylphenyl-methoxy)-7-oxabicyclo-(2,2,1)-heptane; 2-{<3-chloro-5-(trifluoromethyl)-2-pyridinyl>-oxy]-phenoxy}-propanoic acid; ethyl 2-{<3-chloro-5-(trifluoromethyl)-2-pyridinyl>-oxy]-phenoxy}-propanoate; N,N-diisopropyl-S-(2,3,3-trichloroallyl)-thiol-carbamate; 2-chloro-4-ethylamino-6-isopropylamino-1,3,5-triazine; 2-chloro-4-ethylamino-6-(3-cyanopropylamino)-1,3,5-triazine; [(4-amino-3,5-dichloro-6-fluoro-2-pyridinyl)-oxy]-acetic acid; 3,5-dibromo-4-hydroxy-benzonitrile; and methyl 2-[4-(2,4-dichlorophenoxy)-phenoxy]-propanoate is also possible. Surprisingly, some mixtures also exhibit a synergistic action.

Mixing with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

When used in the post-emergent method, the compounds according to the invention can be applied alone or in combination with emulsifiable oils, surface-active substances and other additives.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5.0 kg per ha.

When used as growth regulators, the active compounds according to the invention can be present in the formulations likewise as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultra-low volume method, or to inject the active compound preparation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The amounts used can be varied within a substantial range. In general, 0.01 to 50 kg, preferably 0.05 to 10 kg, of the active compound are employed per hectare of soil surface.

As regards the time of application, the rule is that the growth regulators are applied within a preferred period of time, the exact definition of which depends on the climatic and vegetative circumstances.

The preparation and use of the active compounds according to the invention is evident from the examples below.

PREPARATION EXAMPLES

Example 1

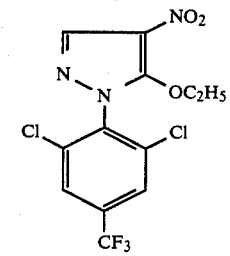
(I-1)

(Process a)

11 g (0.03 mol) of 5-chloro-1-(2,6-dichloro-4-trifluoromethylphenyl)-4-nitro-pyrazole in 30 ml of tetrahydrofuran is added dropwise at 25° C. to a mixture of 1 g of metallic sodium in 30 ml of ethanol and 30 ml of tetrahydrofuran. The reaction mixture is stirred for a further 3 hours at 25° C. and then poured into water, and the aqueous phase is extracted with toluene, dried over sodium sulphate and concentrated in vacuo.

4.1 g (37% of theory) of 1-(2,6-dichloro-4-trifluoromethyl-phenyl)-5-ethoxy-4-nitro-pyrazole of melting point 84°–86° C. are obtained.

Preparation of the starting material

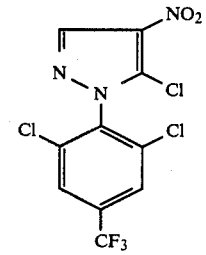
(II-1)

62 g (0.2 mol) of 5-chloro-1-(2,6-dichloro-4-trifluoromethyl-phenyl)-pyrazole are suspended in a mixture of 260 ml of concentrated sulphuric acid and 70 ml of water, and a mixture of 40 ml of concentrated sulphuric acid and 40 ml of concentrated nitric acid are added dropwise at 60° C. When the addition is complete, the mixture is stirred for a further 12 hours at 60° C., cooled and poured onto ice. The reaction product, which deposits as an oil, is taken up in toluene, and the organic phase is washed several times with water and then with sodium hydrogen carbonate solution, and subsequently dried over sodium sulphate. After removing the solvent by distillation in vacuo, the residue is recrystallized from a little petroleum ether.

32 g (44% of theory) of 5-chloro-1-(2,6-dichloro-4-trifluoromethylphenyl)-4-nitro-pyrazole of melting point 80° C.-84° C. are obtained.

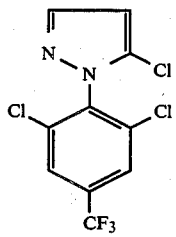

(XII-1)

A mixture of 60 g (0.2 mol) of 1-(2,6-dichloro-4-trifluoromethyl-phenyl)-5-hydroxy-pyrazole and 250 ml of phosphoryl chloride are heated at 160° C. for 20 hours in an autoclave. The cooled reaction batch is subsequently poured onto ice, and the excess phosphoryl chloride is carefully hydrolyzed using sodium hydroxide solution with cooling. The precipitate is filtered off under suction, washed several times with water, and dried.

32 g (51% of theory) of 5-chloro-1-(2,6-dichloro-4-trifluoromethyl-phenyl)-pyrazole of melting point 70° C.-72° C. are obtained.

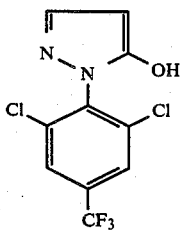

(XVIa-1)

105 g (0.253 mol) of finely powdered diethyl β-(2,6-dichloro-4-trifluoromethyl-phenyl)-hydrazinomethylenemalonate are charged in portions at 80°-85° C. with stirring into a solution of 30 g (0.75 mol) of sodium hydroxide in 1000 ml of water, and the mixture is subsequently stirred for a further 48 hours at 97°-98° C. The cooled reaction mixture is carefully acidified to pH 2 using concentrated hydrochloric acid, and the precipitate thus obtained is filtered off under suction and dried on clay.

100 g (67% of theory) of 5-hydroxy-1-(2,6-dichloro-4-trifluoromethyl-phenyl)-pyrazole of melting point 223° C.-225° C. are obtained.

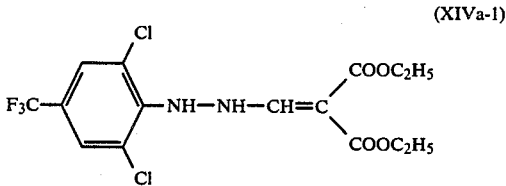

(XIVa-1)

115 g (0.53 mol) of diethyl ethoxymethylenemalonate are added dropwise within 30 minutes at 70° C.-75° C., with stirring, to a solution of 122.5 g (0.5 mol) of 2,6-dichloro-4-trifluoromethyl-phenylhydrazine in 1000 ml of ethanol, and the mixture is stirred, after addition is complete, for a further 5 hours at 70° C. to 75° C. For workup, the solvent is removed in vacuo, and the residue is triturated with water, filtered off under suction and dried on clay.

202 g (97% of theory) of diethyl β-(2,6-dichloro-4-trifluoromethylphenyl)-hydrazinomethylene-malonate of melting point 73° C.-83° C. are obtained.

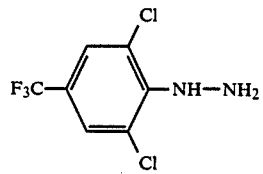

(XIV-1)

6.2 g (0.025 mol) of 3,4,5-trichloro-trifluoromethyl-benzene and 6.25 g (0.125 mol) of hydrazine hydrate are refluxed at 115°-120° C. for 48 hours in 12 ml of pyridine. For work-up, the solvent is removed by distillation, and the residue is taken up in water and extracted three times with about 30 ml of dichloromethane in each case. The combined organic phases are dried over magnesium sulphate, concentrated in vacuo and subsequently distilled.

5.1 g (83% of theory) of 2,6-dichloro-4-trifluoromethylphenylhydrazine of melting point 56° to 57° C. are obtained.

Example 2

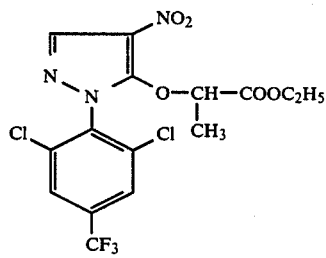

(I-2)

(Process b)

17 g (0.05 mol) of 1-(2,6-dichloro-4-trifluoromethyl-phenyl)-5-(1-ethoxycarbonyl-ethoxy)-pyrazole are dissolved in 50 ml of acetic anhydride, and 10 ml of concentrated nitric acid are added dropwise with stirring at 0°-10° C. within 15 minutes. The reaction batch is stirred for a further 1 hour at room temperature and then poured onto ice water. After neutralization of the mixture using sodium hydrogen carbonate, the organic components are extracted with methylene chloride. The methylene chloride phase is dried over sodium sulphate and concentrated in vacuo. The crude yield of oily reaction product is 17 g. After trituration with petroleum ether, 10.8 g (49% of theory) of 1-(2,6-dichloro-4-trifluoromethylphenyl)-5-(1-ethoxycarbonyl-ethoxy)-4-nitro-pyrazole are obtained in the form of oily crystals.

Preparation of the starting material

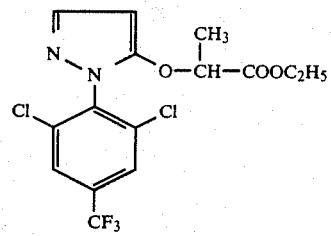 (IV-1)

5.4 g (0.03 mol) of ethyl α-bromopropionate are added to a mixture of 9 g (0.03 mol) of 1-(2,6-dichloro-4-trifluoromethyl-phenyl)-4-H-Δ²-pyrazolin-one and 5.0 g (0.036 mol) of potassium carbonate in 200 ml of acetonitrile, and the batch is stirred for 12 hours at 70° C. The batch is subsequently poured into water, and the organic components are extracted with mehylene chloride, dried over sodium sulphate and concentrated in vacuo. After distillation of the residue, 6 g (50% of theory) of 1-(2,6-dichloro-4-trifluoromethyl-phenyl)-5-(1-ethoxycarbonyl-ethoxy)-pyrazole pass over at 135° C./0.1 Torr as an oil having a refractive index $n_D^{23} = 1.5043$.

Example 3

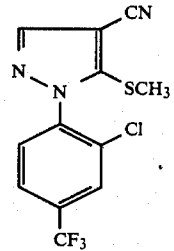 (I-3)

(Process a)

A solution of 3.5 g (0.01 mol) of 5-bromo-1-(2-chloro-4-trifluoromethyl-phenyl)-4-cyano-pyrazole is added dropwise at 20°-25° C. to a suspension of 0.011 mol of potassium methylmercaptide, prepared by passing 0.6 g (0.011 mol) of methyl mercaptan into a solution of 1.4 g (0.012 mol) of potassium t-butylate in 50 ml of tetrahydrofuran. The mixture is stirred overnight, poured into water, and extracted by shaking three times with 100 ml of methylene chloride in each case. After drying the combined phases over sodium sulphate, the solution is concentrated in vacuo. An oily residue remains which crystallizes after standing overnight. 3.1 g (98% of theory) of 1-(2-chloro-4-trifluoromethyl-phenyl)-4-cyano-5-methylthio-pyrazole of melting point 59°-62° C. are obtained.

Preparation of the starting material

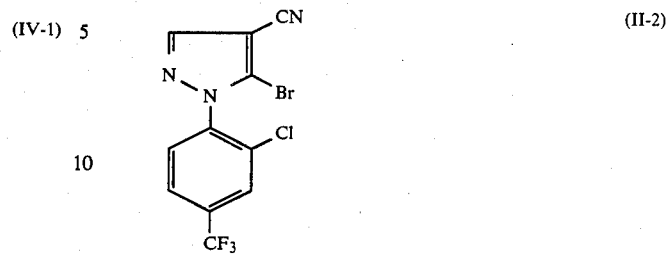 (II-2)

8.6 g (0.03 mol) of 5-amino-1-(2-chloro-4-trifluoromethyl-phenyl)-4-cyano-pyrazole are suspended in 100 ml of 48% strength hydrobromic acid, and a solution of 3.6 g of sodium nitrite in 9 ml of water is added dropwise with stirring at −5° C. to 0° C. When the nitrogen evolution has ceased, the mixture is stirred for a further 6 hours at room temperature, and the precipitate is filtered off under suction, stirred with an aqueous sodium hydrogen carbonate solution, again filtered off under suction, and dried.

10 g (95% of theory) of 5-bromo-1-(2-chloro-4-trifluoromethylphenyl)-4-cyano-pyrazole of melting point 127° C. are obtained.

Example 4

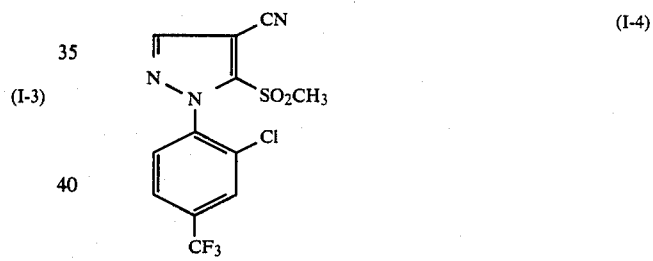 (I-4)

(Process d)

3.2 g (0.01 mol) of 1-(2-chloro-4-trifluoromethyl-phenyl)-4-cyano-5-methylthio-pyrazole (Ex. 1-3) are dissolved in 50 ml of methylene chloride, and a solution of 3.5 g (0.02 mol) of 3-chloroperbenzoic acid in 30 ml of methylene chloride is added at 25° C. The mixture is stirred overnight (about 12 hours), then a further 2 portions of 1.8 g of peracid in each case are added, and the mixture is stirred for a total of 17 hours until starting material can no longer be detected by thin-layer chromatography. The reaction mixture is filtered, and the solution is shaken with saturated sodium thiosulphate solution until peracid can no longer be detected. It is filtered again, the solution is then washed with saturated sodium hydrogen carbonate solution, and the organic phase is dried over sodium sulphate and concentrated in vacuo. The crystalline residue is dissolved in hot toluene. The residue is recrystallized from toluene/petroleum ether. 2.6 g (75% of theory) of 1-(2-chloro-4-trifluoromethyl-phenyl)-4-cyano-5-methanesulphonyl)-pyrazole of melting point 126°-133° C. result.

Example 5

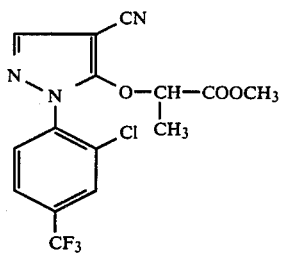

(I-5)

(Process e)

1.1 g (0.011 mol) of methyl lactate are added dropwise to a suspension of 0.4 g (0.11 mol) of sodium hydride in 100 ml of anhydrous tetrahydrofuran. When the hydrogen evolution has ceased, a solution of 3.5 g (0.01 mol) of 1-(2-chloro-4-trifluoromethyl-phenyl)-4-cyano-5-methanesulphonyl-pyrazole (Ex. I-4) in tetrahydrofuran is added dropwise. After stirring at room temperature for 1 hour, some starting pyrazole can still be detected by thin-layer chromatography. After addition of a further 0.04 g of sodium hydride and 0.1 g of methyl lactate and stirring f 2 hours, starting pyrazole can no longer be detected by thin-layer chromatography. The reaction batch is concentrated in vacuo, the residue is distributed between water and methylene chloride, and the methylene chloride phase is washed with water, dried over sodium sulphate and concentrated in vacuo. The oily residue crystallizes overnight. After trituration with petroleum ether and filtering off, 2.3 g (62% of theory) of 1-(2-chloro-4-trifluoromethyl-phenyl)-4-cyano-5-(1-methoxycarbonylethoxy)-pyrazole of melting point 82°–85° C. are obtained.

The following final products of the general formula (I) are obtained corresponding to the preparation examples and according to the general information on processes (a) to (e).

TABLE 2

| Ex. No. | R¹ | R² | R³ | Y | Ar | m.p. (°C.) or ¹HNMR in CDCl₃ in ppm |
|---|---|---|---|---|---|---|
| I-6 | H | NO₂ | CH₃ | O | 2,6-diCl-4-CF₃-phenyl | 81–84 |
| I-7 | CH₃ | NO₂ | CH₃ | O | 2,6-diCl-4-CF₃-phenyl | 2.34(s,3H); 2.58(s,3H); 7.71(s,2H) |
| I-8 | CH₃ | NO₂ | i-C₃H₇ | O | 2,6-diCl-4-CF₃-phenyl | 1.26(d,6H), 2.58(s,3H); 7.71(s,2H) |
| I-9 | H | NO₂ | 4-F-phenyl | O | 2,6-diCl-4-CF₃-phenyl | 6.89(s,2H); 7.0(s,2H); 7.70(s,2H); 8.33(s,1H) |
| I-10 | CH₃ | NO₂ | CH₃ | S | 2,6-diCl-4-CF₃-phenyl | 2.5(s,3H); 2.64(s,3H); 7.74(s,2H) |

TABLE 2-continued

Structure (I):

R¹ at 3-position, R² at 4-position, Y—R³ at 5-position of pyrazole; N1 bears Ar.

| Ex. No. | R¹ | R² | R³ | Y | Ar | m.p. (°C.) or ¹HNMR in CDCl₃ in ppm |
|---|---|---|---|---|---|---|
| I-11 | H | NO₂ | CH₃ | S | 2,6-dichloro-4-(trifluoromethyl)phenyl | 68–72 |
| I-12 | H | NO₂ | —CH₂—COOCH₃ | S | 2,6-dichloro-4-(trifluoromethyl)phenyl | 158–61 |
| I-13 | H | NO₂ | CH₃ | SO₂ | 2,6-dichloro-4-(trifluoromethyl)phenyl | 125–30 |
| I-14 | H | NO₂ | CH₃ | S | 2,4,6-trichlorophenyl | 98 |
| I-15 | H | NO₂ | CH₃ | SO₂ | 2,4,6-trichlorophenyl | 158 |
| I-16 | H | NO₂ | CH₃ | O | 2,4,6-trichlorophenyl | 8.2(s,1H) 4.2(s,3H) O—CH₃ |
| I-17 | H | NO₂ | C₃H₇ | O | 2,4,6-trichlorophenyl | 50–52 |
| I-18 | H | NO₂ | C₂H₅ | O | 2,4,6-trichlorophenyl | 84 |

TABLE 2-continued

General structure (I): pyrazole with R¹ at 3-position, R² at 4-position, Y–R³ at 5-position, Ar on N1.

| Ex. No. | R¹ | R² | R³ | Y | Ar | m.p. (°C.) or ¹HNMR in CDCl₃ in ppm |
|---|---|---|---|---|---|---|
| I-19 | H | NO₂ | -CH(CH₃)-COOC₂H₅ | O | 2,4,6-trichlorophenyl | 89 |
| I-20 | H | NO₂ | C₂H₅ | O | 2-Cl-4-CF₃-phenyl | 96 |
| I-21 | H | NO₂ | C₃H₇ | O | 2-Cl-4-CF₃-phenyl | 8.2(s,1H) pyrazole-H; 4.4(t,2H) —O—C$\underline{H}_2$—C₂H₅ |
| I-22 | H | NO₂ | -CH(CH₃)-COOC₂H₅ | O | 2-Cl-4-CF₃-phenyl | 8.2(s,1H) pyrazole-H; 5.6(q,1H) —O—C$\underline{H}$—CH₃ |
| I-23 | H | CN | -CH(CH₃)-COOC₂H₅ | O | 2-Cl-4-CF₃-phenyl | 7.75(s,1H) pyrazole-H; 5.4(q,1H) —O—C$\underline{H}$—CH₃ |
| I-24 | H | NO₂ | -CH(CH₃)-COOCH₃ | O | 2,6-dichloro-4-CF₃-phenyl | 98 |
| I-25 | H | NO₂ | -CH(CH₃)-COOCH₃ | O | 2,4,6-trichlorophenyl | 84–85 |
| I-26 | H | NO₂ | -CH(CH₃)-COOC₃H₇ | O | 2,6-dichloro-4-CF₃-phenyl | 8.2(s,1H) pyrazole-H; 5.5(q,1H) —O—C$\underline{H}$—CH₃ |

TABLE 2-continued

General structure (I): pyrazole with R¹ at 3-position, R² at 4-position, Y–R³ at 5-position, and Ar on N1.

| Ex. No. | R¹ | R² | R³ | Y | Ar | m.p. (°C.) or ¹HNMR in CDCl₃ in ppm |
|---|---|---|---|---|---|---|
| I-27 | H | NO₂ | —CH(CH₃)—COOC₃H₇ | O | 2,5-dichloro-4-CF₃-phenyl | 8.2(s,1H) pyrazole-H; 5.45(q,1H) —O—CH(CH₃)— |
| I-28 | H | CN | CH₃ | SO₂ | 2-chloro-4-CF₃-phenyl | 85–90 |
| I-29 | H | CN | —CH₂—C₆H₅ | S | 2-chloro-4-CF₃-phenyl | 8.0(s,1H); 4.1(s,2H) —S—CH₂— |
| I-30 | H | CN | —CH₂—C₆H₅ | S | 2-chloro-4-OCF₃-phenyl | 8.1(s,1H); 4.1(q,1H) —O—CH(CH₃)— |
| I-31 | H | NO₂ | —CH(CH₃)—COOC₄H₉ | O | 2,4-dichlorophenyl | 8.25(s,1H); 5.6(q,1H) —O—CH(CH₃)— |
| I-32 | H | NO₂ | —CH(CH₃)—COOC₄H₉ | O | 2,5-dichloro-4-CF₃-phenyl | 8.25(s,1H); 5.5(q,1H) —O—CH(CH₃)— |
| I-33 | H | CN | —CH(CH₃)—COOC₂H₅ | O | 2-chloro-4-OCF₃-phenyl | 7.75(s,1H); 5.4(q,1H) —O—CH(CH₃)— |
| I-34 | H | NO₂ | —CH(CH₃)—COOCH₃ | O | 2-chloro-4-CF₃-phenyl | 8.25(s,1H); 5.6(q,1H) —O—CH(CH₃)— |

TABLE 2-continued $$\underset{Ar}{\underset{|}{N-N}}\overset{R^1}{\underset{\phantom{N}}{\diagup}}\overset{R^2}{\underset{\phantom{N}}{\diagdown}}Y-R^3 \quad (I)$$

| Ex. No. | R¹ | R² | R³ | Y | Ar | m.p. (°C.) or ¹HNMR in CDCl₃ in ppm |
|---|---|---|---|---|---|---|
| I-35 | H | CN | CH₃ | O | 2-Cl, 4-OCF₃-phenyl | 70 |
| I-36 | H | CN | C₂H₅ | O | 2-Cl, 4-OCF₃-phenyl | 7.75(s,1H); 4.65 —O—C$\underline{H}_2$—CH₃ |
| I-37 | H | CN | CH₃ | O | 2-Cl, 4-CF₃-phenyl | 104 |
| I-38 | H | CN | —CH(CH₃)—COOCH₃ | O | 2-Cl, 4-OCF₃-phenyl | 74–78 |
| I-39 | H | CN | —CH(CH₃)—COOC₄H₉ | O | 2-Cl, 4-OCF₃-phenyl | 7.75(s,1H); 5.45(q,1H) —O—C$\underline{H}$—CH₃ |
| I-40 | H | CN | —CH₂—COOC₄H₉ | O | 2-Cl, 4-OCF₃-phenyl | 7.8(s,1H); 5.0(s,2H) —O—C$\underline{H}_2$— |
| I-41 | H | NO₂ | —CH₂—COOC₄H₉ | O | 2,4,6-triCl-phenyl | 8.3(s,1H); 5.05(s,2H) —O—C$\underline{H}_2$— |
| I-42 | H | NO₂ | —CH(CH₃)—COOC₂H₅ | O | 2,6-diCl, 4-CF₃-phenyl | 8.25(s,1H); 5.45(m,1H) —O—C$\underline{H}$—CH₃ |
| I-43 | H | NO₂ | —CH(CH₃)—COOC₃H₇ | O | 2,6-diCl, 4-CF₃-phenyl | 8.25(s,1H); 5.5(m,1H) —O—C$\underline{H}$—CH₃ |

TABLE 2-continued

Structure (I): Pyrazole with R¹ at 3-position, R² at 4-position, Y-R³ at 5-position, and Ar on N1.

| Ex. No. | R¹ | R² | R³ | Y | Ar | m.p. (°C.) or ¹HNMR in CDCl₃ in ppm |
|---|---|---|---|---|---|---|
| I-44 | H | NO₂ | CH₃ | S | 2-Cl-4-CF₃-phenyl | 8.45(s,1H) 2.5(s,3H) —S—CH₃ |
| I-45 | H | NO₂ | —CH(CH₃)—COOCH₃ | O | 2,3-diCl-4-CF₃-phenyl | 83 |
| I-46 | H | NO₂ | —CH(CH₃)—COO(CH₂)₂CH₃ | O | 2-Cl-4-CF₃-phenyl | ¹H—NMR*: 8.2; 5.6. |
| I-47 | H | CN | —CH₂—C₆H₅ | SO | 2-Cl-4-OCF₃-phenyl | 109°–116° C. |
| I-48 | H | CN | CH₃ | S | 2,4-diCl-phenyl | 84°–91° C. |
| I-49 | H | CN | CH₃ | SO₂ | 2,6-diCl-4-CF₃-phenyl | 154°–156° C. |
| I-50 | H | NO₂ | —(CH₂)₃—CH₃ | O | 2-Cl-4-CF₃-phenyl | ¹H—NMR*: 8.1; 4.4. |
| I-51 | H | CN | —C₆H₅ | O | 2-Cl-4-CF₃-phenyl | 118°–120° C. |
| I-52 | H | CN | 3-CF₃-phenyl | O | 2-Cl-4-CF₃-phenyl | 117°–121° C. |

TABLE 2-continued

Structure (I):

$R^1$ at 3-position, $R^2$ at 4-position of pyrazole; N1 bears Ar; 5-position bears $Y-R^3$.

| Ex. No. | $R^1$ | $R^2$ | $R^3$ | Y | Ar | m.p. (°C.) or $^1$HNMR in CDCl$_3$ in ppm |
|---|---|---|---|---|---|---|
| I-53 | H | CN | C$_2$H$_5$ | O | 2-Cl-4-CF$_3$-C$_6$H$_3$ | 100° C. |
| I-54 | H | CN | —CH(CH$_3$)—COO—(CH$_2$)$_3$—CH$_3$ | O | 2-Cl-4-CF$_3$-C$_6$H$_3$ | $^1$HNMR*: 7.8; 5.4. |
| I-55 | H | CN | —CH(CH$_3$)—CO—NH—(CH$_2$)$_2$—CH$_3$ | O | 2-Cl-4-CF$_3$-C$_6$H$_3$ | 78°–87° C. |
| I-56 | H | CN | —CH(CH$_3$)—CO—NH—(CH$_2$)$_3$—CH$_3$ | O | 2,6-diCl-4-CF$_3$-C$_6$H$_2$ | 87°–94° C. |
| I-57 | H | CN | —CH(CH$_3$)—CO—NH—CH$_3$ | O | 2,6-diCl-4-CF$_3$-C$_6$H$_2$ | 122°–129° C. |
| I-58 | H | CN | —CH(CH$_3$)—CO—NH—C$_2$H$_5$ | O | 2,6-diCl-4-CF$_3$-C$_6$H$_2$ | 112°–117° C. |
| I-59 | H | CN | —CH(CH$_3$)—COO—(CH$_2$)$_2$—CH$_3$ | O | 2,6-diCl-4-CF$_3$-C$_6$H$_2$ | $^1$H—NMR*: 7.9; 5.4. |
| I-60 | H | CN | —CH(CH$_3$)—CO—NH—CH$_2$—CH=CH$_2$ | O | 2,6-diCl-4-CF$_3$-C$_6$H$_2$ | 88°–91° C. |
| I-61 | (CH$_3$)$_3$C— | NO$_2$ | CH$_3$ | S | 2,6-diCl-4-CF$_3$-C$_6$H$_2$ | $^1$H—NMR*: 7.78 |

TABLE 2-continued

Structure (I):

$R^1$, $R^2$ on pyrazole; $N-N-Ar$; $Y-R^3$

| Ex. No. | $R^1$ | $R^2$ | $R^3$ | Y | Ar | m.p. (°C.) or $^1$HNMR in CDCl$_3$ in ppm |
|---|---|---|---|---|---|---|
| I-62 | (CH$_3$)$_3$C— | NO$_2$ | C$_2$H$_5$ | O | 2,6-Cl$_2$-4-CF$_3$-C$_6$H$_2$ | $^1$H—NMR*: 7.76 |
| I-63 | F$_3$C— | NO$_2$ | C$_2$H$_5$ | O | 2,4,6-Cl$_3$-C$_6$H$_2$ | 112°–115° C. |

*The $^1$H—NMR—Spectra are done in CDCl$_3$ with tetramethylsilan as inner standard. The chemical shift is given as δ-value in ppm.

The following precursors of the general formula (IV) are obtained corresponding to preparation Example 2 and according to the general information for the preparation

TABLE 3

Structure (IV):

$R^1$ on pyrazole; $N-N-Ar$; $Y^1-R^3$

| Ex. No. | $R^1$ | $R^3$ | $Y^1$ | Ar | m.p. (°C.) or $^1$HNMR in CDCl$_3$ in ppm |
|---|---|---|---|---|---|
| IV-2 | H | CH$_3$ | O | 2,6-Cl$_2$-4-CF$_3$-C$_6$H$_2$ | 84–87 |
| IV-3 | H | i-C$_3$H$_7$ | O | 2,4,6-Cl$_3$-C$_6$H$_2$ | 30–35 |
| IV-4 | H | $-\mathrm{CH(CH_3)-COOCH_3}$ | O | 2,6-Cl$_2$-4-CF$_3$-C$_6$H$_2$ | 5.6(d, 1H) [pyrazole H]; 4.7(q, 1H) —O—CH(CH$_3$)— |

TABLE 3-continued $$\text{(IV)}$$

Pyrazole structure with $R^1$ at 3-position, $Y^1-R^3$ at 5-position, Ar on N1.

| Ex. No. | $R^1$ | $R^3$ | $Y^1$ | Ar | m.p. (°C.) or $^1$HNMR in CDCl$_3$ in ppm |
|---------|-------|-------|-------|-----|------|
| IV-5 | H | $-\underset{\mid}{\overset{CH_3}{CH}}-COOC_2H_5$ | O | 2,6-dichloro-4-(CF$_3$)phenyl | 5.6(d, 1H) pyrazole-H; 4.7(q, 1H) $-O-\underline{CH}(CH_3)-$ |
| IV-6 | H | $-\underset{\mid}{\overset{CH_3}{CH}}-COOC_3H_7$ | O | 2,6-dichloro-4-(CF$_3$)phenyl | 5.6(d, 1H) pyrazole-H; 4.7(q, 1H) $-O-\underline{CH}(CH_3)-$ |
| IV-7 | H | $-\underset{\mid}{\overset{CH_3}{CH}}-COOC_4H_9$ | O | 2,6-dichloro-4-(CF$_3$)phenyl | 5.6(d, 1H) pyrazole-H; 4.7(q, 1H) $-O-\underline{CH}(CH_3)-$ |
| IV-8 | H | $-CH_2-COOC_2H_5$ | O | 2,6-dichloro-4-(CF$_3$)phenyl | 5.6(d, 1H) pyrazole-H; 4.6(s, 2H) $-O-\underline{CH_2}-$ |
| IV-9 | H | $-\underset{\mid}{\overset{CH_3}{CH}}-COOCH_3$ | O | 2,4,6-trichlorophenyl | 98 |
| IV-10 | H | $-\underset{\mid}{\overset{CH_3}{CH}}-COOC_2H_5$ | O | 2,4,6-trichlorophenyl | 54 |

TABLE 3-continued $$\text{(IV)}$$

Structure (IV): pyrazole with $R^1$ at 3-position, $Y^1-R^3$ at 5-position, Ar on N1.

| Ex. No. | $R^1$ | $R^3$ | $Y^1$ | Ar | m.p. (°C.) or $^1$HNMR in CDCl$_3$ in ppm |
|---|---|---|---|---|---|
| IV-11 | H | $-\underset{\underset{CH_3}{\mid}}{CH}-COOC_3H_7$ | O | 2,4,6-trichlorophenyl | 5.6(d, 1H) pyrazole-H; 4.7(q, 1H) $-O-\underline{CH}(CH_3)-$ |
| IV-12 | H | $-\underset{\underset{CH_3}{\mid}}{CH}-COOC_4H_9$ | O | 2,4,6-trichlorophenyl | 5.6(d, 1H) pyrazole-H; 4.7(q, 1H) $-O-\underline{CH}(CH_3)-$ |
| IV-13 | H | $-CH_2-COOC_2H_5$ | O | 2,4,6-trichlorophenyl | 5.6(d, 1H) pyrazole-H; 4.6(s, 2H) $-O-\underline{CH_2}-$ |
| IV-14 | H | $-\underset{\underset{CH_3}{\mid}}{CH}-COOCH_3$ | O | 2-chloro-4-trifluoromethylphenyl | 5.6(d, 1H) pyrazole-H; 4.7(q, 1H) $-O-\underline{CH}(CH_3)-$ |
| IV-15 | H | $-\underset{\underset{CH_3}{\mid}}{CH}-COOC_2H_5$ | O | 2-chloro-4-trifluoromethylphenyl | 5.6(d, 1H) pyrazole-H; 4.7(q, 1H) $-O-\underline{CH}(CH_3)-$ |
| IV-16 | H | $-\underset{\underset{CH_3}{\mid}}{CH}-COOC_3H_7$ | O | 2-chloro-4-trifluoromethylphenyl | 5.6(d, 1H) pyrazole-H; 4.7(q, 1H) $-O-\underline{CH}(CH_3)-$ |

TABLE 3-continued $$(IV)$$

Structure (IV): pyrazole with R¹ at 3-position, N–N, N-Ar, 5-position Y¹–R³

| Ex. No. | R¹ | R³ | Y¹ | Ar | m.p. (°C.) or ¹HNMR in CDCl₃ in ppm |
|---|---|---|---|---|---|
| IV-17 | H | –CH(CH₃)–COOC₄H₉ | O | 2-Cl, 4-CF₃-phenyl | 5.6 (d, 1H) pyrazole-H; 4.7 (q, 1H) –O–CH(CH₃)– |
| IV-18 | H | –CH₂–COOC₂H₅ | O | 2-Cl, 4-CF₃-phenyl | 5.6 (d, 1H) pyrazole-H; 4.6 (s, 2H) –O–CH₂– |
| IV-19 | H | –CH(CH₃)–COOCH₃ | O | 2,3,5-trichloro-4-CF₃-phenyl | 5.6 (d, 1H) pyrazole-H; 1.55 (d, 3H) –O–CH(CH₃)– |
| IV-20 | CH₃ | CH₃ | O | 2,6-dichloro-4-CF₃-phenyl | 2.28 (s, 3H) 3-CH₃ pyrazole; 5.48 (s, 1H) pyrazole-H; 3.83 (s, 3H) –O–CH₃ |
| IV-21 | CH₃ | C₂H₅ | O | 2,6-dichloro-4-CF₃-phenyl | $n_{23}^D = 1.5166$ |

TABLE 3-continued

Formula (IV):

| Ex. No. | R¹ | R³ | Y¹ | Ar | m.p. (°C.) or ¹HNMR in CDCl₃ in ppm |
|---|---|---|---|---|---|
| IV-22 | $CH_3$ | $i\text{-}C_3H_7$ | O | 2,6-dichloro-4-trifluoromethylphenyl | $n_{23}^D = 1.5093$ |
| IV-23 | H | $-\underset{CH_3}{\underset{|}{CH}}-COOC_2H_5$ | O | 2,3,5-trichloro-4-trifluoromethylphenyl... (Cl, Cl, CF₃, Cl) | 8.25(s, 1H) pyrazole H; 5.45(m, 1H) $-O-\underset{CH_3}{\underset{|}{CH}}-$ |
| IV-24 | H | $-\underset{CH_3}{\underset{|}{CH}}-COOC_3H_7$ | O | 2,3,5-trichloro-4-trifluoromethylphenyl | 8.25(s, 1H); 5.5 (m, 1H) $-O-\underset{CH_3}{\underset{|}{CH}}-$ |
| IV-25 | H | $CH_3$ | S | 2,6-dichloro-4-trifluoromethylphenyl | 69 |

PREPARATION OF THE PRECURSORS OF THE FORMULA (V)

Example (V-1)

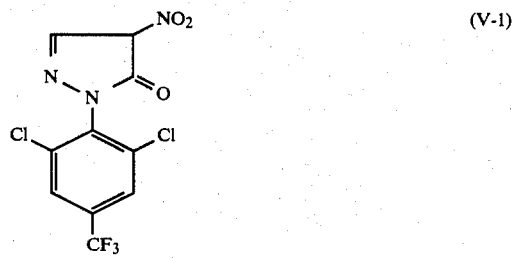

(V-1)

9 g (0.03 mol) of 1-(2,6-dichloro-4-trifluoromethyl-phenyl)-pyrazol-5-one are finely powdered and charged in portions into a mixture of 40 ml of water and 20 ml of nitric acid (d=1.5). Stirring is continued overnight, and the solid product is then filtered off under suction, washed with water and dried. For purification, the product is triturated with ligroin, filtered off under suction and dried.

2.2 g (21% of theory) of 1-(2,6-dichloro-4-trifluoromethyl-phenyl)-4-nitro-pyrazol-5-one of melting point 100°–108° C. are obtained.

Example (V-2)

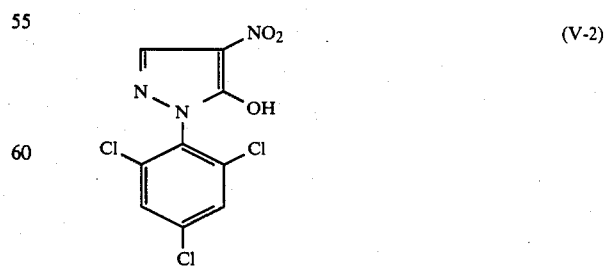

(V-2)

3.3 g of 1-(2,4,6-trichlorophenyl)-4-nitro-5-chloropyrazole are suspended in 10 ml of methanol, and 20 ml of 1N methanolic potassium hydroxide solution are added. The mixture is refluxed for 12 hours. In order to achieve complete reaction, a further 10 ml of 1N methanolic potassium hydroxide solution are added to the reaction mixture, which is refluxed for a further 12 hours. For work-up, the mixture is filtered, the solvent is stripped off in vacuo, the residue is taken up in hot water, and the product is precipitated by acidification with 2N hydrochloric acid. After filtering off and drying, 1.5 g (49% of theory) of 1-(2,4,6-trichlorophenyl)-4-nitro-5-hydroxypyrazole of melting point 106°–115° C. are obtained.

The following precursor of the general formula (V) is obtained in a corresponding fashion and according to the general information for the preparation:

TABLE 4

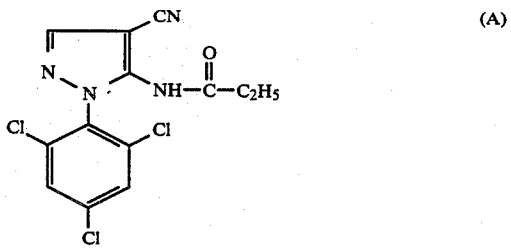

| Ex. No | $R^1$ | $R^2$ | $Y^1$ | Ar | m.p. (°C.) |
|---|---|---|---|---|---|
| V-3 | H | CN | O | (3-Cl, 5-CF$_3$ phenyl) | 210–13 |

USE EXAMPLES

In the following use examples, the compound shown below as employed as comparison substance:

(A) — pyrazole structure with CN, NH—C(=O)—C$_2$H$_5$, and 2,4,6-trichlorophenyl group (known from DE-OS (German Published Specification) No. 3,226,513)

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the state amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the compound according to Preparation Example: 1–6, for example, exhibits a marked superiority in the crop plant selectivity, particularly in wheat, cotton and corn, compared to the comparison substance (A).

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the compound according to Preparation Example: 1–6, for example, exhibits a marked superiority in the crop plant selectivity, particularly in wheat and barley, compared to the comparison substance (A).

EXAMPLE C

Defoliation and desiccation of the leaves of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:

0 denotes no desiccation of leaves, no shedding of leaves

+ denotes slight desiccation of the leaves, slight shedding of leaves

++ denotes severe desiccation of the leaves, severe shedding of leaves

+++ denotes very severe desiccation of the leaves, very severe shedding of leaves In this test, the compounds according to Preparation Examples I-11, I-16, I-22, I-23, I-25, I-26, I-31, I-33, I-34, I-38 and I-39, for example, exhibit a marked activity compared to the untreated control.

It is understood that the specification and examples are illustrative but not limitative of the present inven-

We claim:

1. A 4-cyano(nitro)-5-oxy(thio)-pyrazole of the formula

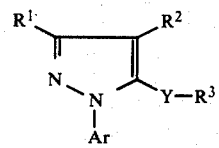

in which
R¹ represents hydrogen, straight-chain or branched alkyl having 1 to 4 carbon atoms, or straight-chain or branched halogenoalkyl having 1 to 4 carbon atoms and 1 to 9 identical or different halogen atoms,
R² represents nitro or cyano,
R³ represents alkyl, alkenyl or alkinyl in each case having up to 6 carbon atoms and optionally substituted by halogen; alkoxy, alkylthio, alkylsulphinyl, alkylsulphonyl or dialkoxy in each case having 1 to 4 carbon atoms in the alkyl parts; cyano; hydroxycarbonyl; alkoxycarbonyl, alkylthiocarbonyl or alkylcarbonyl in each case having 1 to 4 carbon atoms in the alkyl part; aminocarbonyl; alkylaminocarbonyl or dialkylaminocarbonyl in each case having 1 to 4 carbon atoms in the alkyl parts; hydroxyimino or alkoximino having 1 to 4 carbon atoms; or the

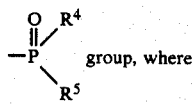

group, where

R⁴ and R⁵ are identical or different and represent hydroxyl, alkyl or alkoxy in each case having 1 to 4 carbon atoms, or also phehyl or phenoxy which are in each case optionally mono- or polysubstituted by those substituents recited as phenyl or pyridyl substituents for Ar hereinbelow; or
R³ represents cycloalkyl or cycloalkylalkyl, having 3 to 7 carbon atoms in the cycloalkyl part and 1 to 2 carbon atoms in the alkyl part, which are in each case optionally substituted in the cycloalkyl part by halogen, alkyl, alkoxy or alkylthio in each case having 1 to 4 carbon atoms; or represents phenyl or phenylalkyl, having 1 to 4 carbon atoms in the straight-chain or branched alkyl part, which are in each case optionally substituted on the phenyl by halogen, cyano, nitro, in each case straight-chain or branched alkyl, alkoxy, alkylthio, alkylsulphinyl, alkylsulphonyl, halogenoalkyl, halogenoalkoxy, halogenoalkylthio, halogenoalkylsulphinyl or halogenoalkylsulphonyl in each case having 1 to 4 carbon atoms in the individual alkyl parts and, if appropriate, 1 to 9 identical or different halogen atoms;
Ar represents phenyl which is substituted twice or more, or 2-pyridyl, 3-pyridyl or 4-pyridyl which phenyl or pyridyl is in each case optionally substituted by cyano, nitro, halogen, in each case straight-chain or branched alkyl, alkoxy or alkoxycarbonyl in each case having up to 4 carbon atoms, in addition in each case straight-chain or branched halogenoalkyl or halogenoalkoxy in each case having up to 4 carbon atoms and up to 9 identical or different halogen atoms, or a —S(U)ₘR⁶ radical where
R⁶ represents amino, or also in each case straight-chain or branched alkyl alkylamino, dialkylamino or halogenoalkyl in each case having up to 4 carbon atoms in the individual alkyl parts and, in the case of halogenoalkyl, having up to 9 identical or different halogen atoms, and
m represents a number 0, 1 or 2, and
Y represents O, S, SO or SO₂.

2. A 4-cyano(nitro)-5-oxy(thio)-pyrazole according to claim 1,
in which
R¹ represents hydrogen, methyl, ethyl, n- or i-propyl or trifluoromethyl;
R² represents nitro or cyano;
R³ represents methyl, ethyl; n- or i-propyl; n-, i-, s- or t-butyl; n- or i-pentyl; n- or i-hexyl, allyl, propenyl, butenyl, propargyl or butinyl, which may in each case be mono- or poly-substituted by fluorine, chlorine, bromine, methoxy, ethoxy, methylthio, ethylthio, methylsulphinyl, methylsulphonyl, dimethoxy, diethoxy, cyano, hydroxycarbonyl, methoxycarbonyl, ethoxycarbonyl, propoxycarbonyl, butoxycarbonyl, aminocarbonyl, methylaminocarbonyl, dimethylaminocarbonyl, methylthiocarbonyl, methylcarbonyl, hydroximino, methoximino, ethoximino, phosphonyl, methylphosphinoyl, dimethylphosphinoyl, methyl-ethyl-phosphinoyl, dimethylphosphonoyl and diethylphosphonoyl, the substituents being identical or different, furthermore represents cyclopropyl, cyclopentyl, cyclohexyl, cyclopropylmethyl, cyclopentylmethyl or cyclohexylmethyl which may in each case be mono- or disubstituted by fluorine, chlorine or methyl, the substituents being identical or different; or represents phenyl, benzyl or phenylethyl which are in each case optionally mono- to trisubstituted on the phenyl by fluorine, chlorine, bromine, iodine, cyano, nitro, methyl, ethyl, methoxy, methylthio, trifluoromethyl, methylsulphinyl, methylsulphonyl, trifluoromethoxy, trifluoromethylthio, trifluoromethylsulphinyl and trifluoromethylsulphonyl; and
Ar represents phenyl which is substituted twice or more, and also 2-pyridyl, 3-pyridyl or 4-pyridyl which are in each case optionally mono- to tetrasubstituted, the substituents being identical or different, the phenyl or pyridyl substituents being cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, dichlorofluoromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an
—S(O)$_m$R$^6$ radical, where
R$^6$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, and
m represents a number 0, 1 or 2.

3. A compound according to claim 1, wherein such compound is 1-2,6-dichloro-4-trifluoromethyl-phenyl)-5-methoxy-4-nitro-pyrazole of the formula

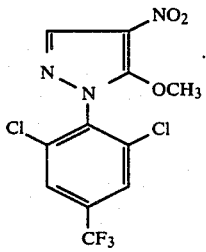

4. A compound according to claim 1, wherein such compound is 1-(2,6-dichloro-4-trifluoromethyl-phenyl)-5-methylthio-4-nitro-pyrazole of the formula

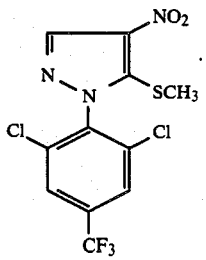

5. A compound according to claim 1, wherein such compound is 1-(2,4,6-trichloro-phenyl)-5-methoxy-4-nitro-pyrazole of the formula

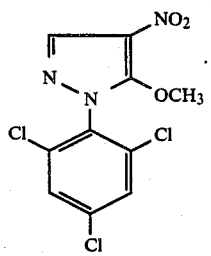

6. A compound according to claim 1, wherein such compound is 1-(2-chloro-4-trifluoromethyl-phenyl)-5-(1-ethoxycarbonylethoxy)-4-nitro-pyrazole of the formula

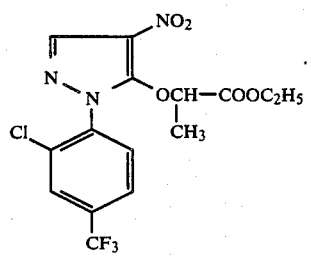

7. A compound according to claim 1, wherein such compound is 1-(2-chloro-4-trifluoromethyl-phenyl)-5-(1-ethoxycarbonylethoxy)-4-cyano-pyrazole of the formula

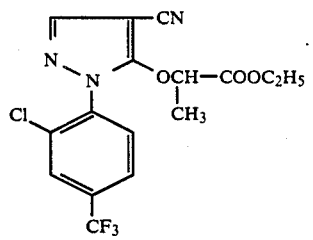

8. A compound according to claim 1, wherein such compound is 1-(2,4,6-trichloro-phenyl)-5-(1-ethoxycarbonylethoxy)-4-nitro-pyrazole of the formula

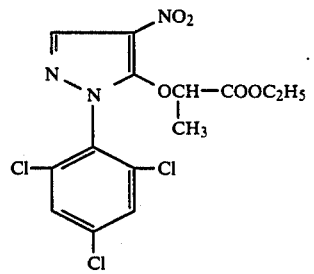

9. A compound according to claim 1, wherein such compound is 1-(2,6-dichloro-4-trifluoromethyl-phenyl)-5-(1-propoxy-carbonyl-ethoxy)-4-nitro-pyrazole of the formula

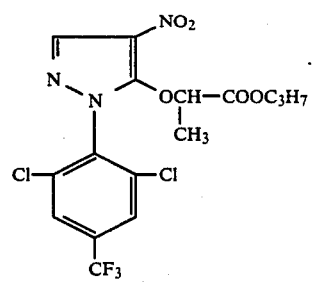

10. A compound according to claim 1, wherein such compound is 1-(2,4-dichloro-phenyl)-5-(1-butoxycarbonyl-ethoxy)-4-nitro-pyrazole of the formula

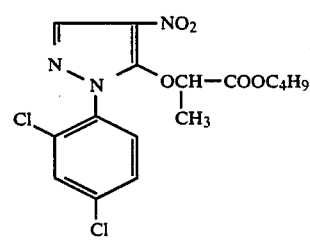

11. A compound according to claim 1, wherein such compound is 1-(2-chloro-4-trifluoromethoxy-phenyl)-5-(1-ethoxycarbonylethoxy)-4-cyano-pyrazole of the formula

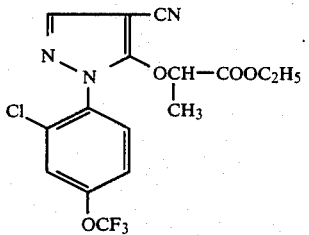

12. A compound according to claim 1, wherein such compound is 1-(2-chloro-4-trifluoromethyl-phenyl)-5-(1-methoxycarbonylethoxy)-4-nitro-pyrazole of the formula

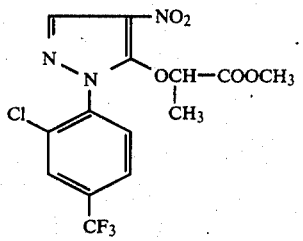

13. A compound according to claim 1, wherein such compound is 1-(2-chloro-4-trifluoromethoxy-phenyl)-5-(1-methoxycarbonylethoxy)-4-cyano-pyrazole of the formula

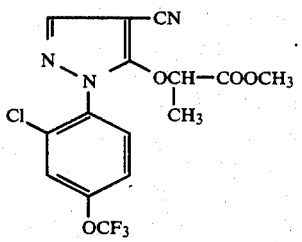

14. A compound according to claim 1, wherein such compound is 1-(2-chloro-4-trifluoromethoxy-phenyl)-5-(1-butoxycarbonylethoxy)-4-cyano-pyrazole of the formula

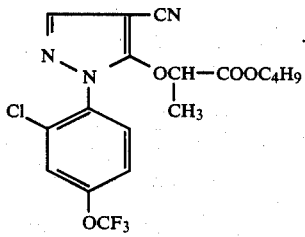

15. A herbicidal composition comprising a herbicidally effective amount of a compound according to claim 1 and a diluent.

16. A method of combating unwanted vegetation which comprises applying to such vegetation or to a locus from which it is desired to exclude such vegetation a herbicidally effective amount of a compound according to claim 1.

17. The method according to claim 16, wherein such compound is
1-(2,6-dichloro-4-trifluoromethyl-phenyl)-5-methoxy-4-nitro-pyrazole,
1-(2,6-dichloro-4-trifluoromethyl-phenyl)-5-methylthio-4-nitro-pyrazole,
1-(2,4,6-trichloro-phenyl)-5-methoxy-4-nitro-pyrazole,
1-(2-chloro-4-trifluoromethyl-phenyl)-5-(1-ethoxycarbonyl-ethoxy)-4-nitro-pyrazole,
1-(2-chloro-4-trifluoromethyl-phenyl)-5-(1-ethoxycarbonyl-ethoxy)-4-cyano-pyrazole,
1-(2,4,6-trichloro-phenyl)-5-(1-ethoxycarbonylethoxy)-4-nitro-pyrazole,
1-(2,6-dichloro-4-trifluoromethyl-phenyl)-5-(1-propoxycarbonyl-ethoxy)-4-nitro-pyrazole,
1-(2,4-dichloro-phenyl)-5-(1-butoxycarbonyl-ethoxy)-4-nitro pyrazole,
1-(2-chloro-4-trifluoromethoxy-phenyl)-5-(1-ethoxycarbonyl-ethoxy)-4-cyano-pyrazole,
1-(2-chloro-4-trifluoromethyl-phenyl)-5-(1-methoxycarbonyl-ethoxy)-4-nitro-pyrazole,
1-(2-chloro-4-trifluoromethoxy-phenyl)-5-(1-methoxycarbonyl-ethoxy)-4-cyano-pyrazole or
1-(2-chloro-4-trifluoromethoxy-phenyl)-5-(1-butoxycarbonyl-ethoxy)-4-cyano-pyrazole.

18. A plant-growth regulating composition comprising a plant-growth regulating effective amount of a compound according to claim 1 and a diluent.

19. A method of regulating the growth of plants which comprises applying to such plants or to a locus in which such plants are growing or are to be grown a plant-growth regulating effective amount of a compound according to claim 1.

20. The method according to claim 19, wherein such compound
1-(2,6-dichloro-4-trifluoromethyl-phenyl)-5-methoxy-4-nitro-pyrazole,
1-(2,6-dichloro-4-trifluoromethyl-phenyl)-5-methylthio-4-nitro-pyrazole,
1-(2,4,6-trichloro-phenyl)-5-methoxy-4-nitro-pyrazole,
1-(2-chloro-4-trifluoromethyl-phenyl)-5-(1-ethoxycarbonyl-ethoxy)-4-nitro-pyrazole,
1-(2-chloro-4-trifluoromethyl-phenyl)-5-(1-ethoxycarbonyl-ethoxy)-4-cyano-pyrazole,
1-(2,4,6-trichloro-phenyl)-5-(1-ethoxycarbonylethoxy)-4-nitro-pyrazole,
1-(2,6-dichloro-4-trifluoromethyl-phenyl)-5-(1-propoxycarbonyl-ethoxy)-4-nitro-pyrazole,
1-(2,4-dichloro-phenyl-5-(1-butoxycarbonyl-ethoxy)-4-nitro pyrazole,
1-(2-chloro-4-trifluoromethoxy-phenyl)-5-(1-ethoxycarbonyl-ethoxy)-4-cyano-pyrazole,
1-(2-chloro-4-trifluoromethyl-phenyl)-5-(1-methoxycarbonyl-ethoxy)-4-nitro-pyrazole,
1-(2-chloro-4-trifluoromethoxy-phenyl)-5-(1-methoxycarbonyl-ethoxy)-4-cyano-pyrazole or
1-(2-chloro-4-trifluoromethoxy-phenyl)-5-(1-butoxycarbonyl-ethoxy)-4-cyano-pyrazole.

* * * * *

UNITED STATES PATENT AND TRADEMARK OFFICE
CERTIFICATE OF CORRECTION

PATENT NO. : 4,770,692

DATED : September 13, 1988

INVENTOR(S) : Jörg Stetter, et al

It is certified that error appears in the above-identified patent and that said Letters Patent is hereby corrected as shown below:

| | |
|---|---|
| Col. 2, line 62 and Col. 3, line 23 | Delete "$Y_1$" and substitute --$Y^1$-- |
| Col. 6, line 8-9 | Delete "methoxyimino" and substitute --methoximino-- |
| Col. 20, line 55 | Delete "nitrile" and substitute --nitrite-- |
| Col. 21, line 55 | Before "diluent" insert --a-- |
| Col. 22, line 42 | Correct --arylhydrazines-- |
| Col. 28, line 9 | After "extenders" delete "of" and substitute --or-- |
| Col. 28, line 23 | Delete "sheels" and substitute --shells-- |
| Col. 29, line 5 | After "N-" delete " } " and substitute -- { -- |
| Col. 51, under Ex. No. IV-6 | Delete "0" |
| Col. 59, line 35 | After "below" delete "as" and substitute --was-- |
| Col. 59, line 58 | Delete "state" and substitute --stated-- |
| Col. 61, line 42 | Delete "phehyl" and substitute --phenyl-- |
| Col. 62, line 4 | Delete "-$S(U)_m R^6$" and substitute -- -$S(O)_m R^6$ -- |

UNITED STATES PATENT AND TRADEMARK OFFICE
CERTIFICATE OF CORRECTION

PATENT NO. : 4,770,692
DATED : September 13, 1988
INVENTOR(S) : Jörg Stetter, et al Page 2 of 2

It is certified that error appears in the above-identified patent and that said Letters Patent is hereby corrected as shown below:

Col. 63, line 9         Delete "1-2,6-" and substitute --1-(2,6- --

Col. 66, line 39        After "compound" insert --is--

Signed and Sealed this

Twenty-third Day of May, 1989

Attest:

DONALD J. QUIGG

Attesting Officer       Commissioner of Patents and Trademarks